US010736969B2

(12) United States Patent
Cheng et al.

(10) Patent No.: US 10,736,969 B2
(45) Date of Patent: Aug. 11, 2020

(54) MULTI-ARM POLYMERIC PRODRUG CONJUGATES OF PEMETREXED-BASED COMPOUNDS

(75) Inventors: Lin Cheng, Sunnyvale, CA (US); Jennifer Riggs-Sauthier, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 1899 days.

(21) Appl. No.: 13/995,415

(22) PCT Filed: Dec. 21, 2011

(86) PCT No.: PCT/US2011/066510
§ 371 (c)(1),
(2), (4) Date: Sep. 6, 2013

(87) PCT Pub. No.: WO2012/088282
PCT Pub. Date: Jun. 28, 2012

(65) Prior Publication Data
US 2013/0338175 A1    Dec. 19, 2013

Related U.S. Application Data

(60) Provisional application No. 61/425,728, filed on Dec. 21, 2010.

(51) Int. Cl.
*A61K 47/60* (2017.01)

(52) U.S. Cl.
CPC .................................. *A61K 47/60* (2017.08)

(58) Field of Classification Search
CPC .............................................. A61K 47/48215
See application file for complete search history.

(56) References Cited

U.S. PATENT DOCUMENTS

| | | | |
|---|---|---|---|
| 4,670,417 A | 6/1987 | Iwasaki et al. | |
| 5,217,974 A | 6/1993 | Grindey et al. | |
| 5,252,714 A | 10/1993 | Harris et al. | |
| 5,281,698 A | 1/1994 | Nitecki | |
| 5,344,932 A | 9/1994 | Taylor | |
| 5,468,478 A | 11/1995 | Saifer et al. | |
| 5,629,384 A | 5/1997 | Veronese et al. | |
| 5,650,234 A | 7/1997 | Dolence et al. | |
| 5,672,662 A | 9/1997 | Harris et al. | |
| 5,824,784 A | 10/1998 | Kinstler et al. | |
| 5,880,131 A | 3/1999 | Greenwald et al. | |
| 5,900,461 A | 5/1999 | Harris | |
| 6,461,603 B2 | 10/2002 | Bentley et al. | |
| 7,026,440 B2 | 4/2006 | Bentley et al. | |
| 7,744,861 B2 | 6/2010 | Zhao et al. | |
| 7,772,209 B2 | 8/2010 | Niyikiza | |
| 2006/0105046 A1 | 5/2006 | Bentley et al. | |
| 2006/0275252 A1* | 12/2006 | Harris | A61K 47/48215 424/78.27 |
| 2007/0025956 A1 | 2/2007 | Burton et al. | |
| 2009/0074704 A1* | 3/2009 | Zhao | A61K 47/48192 424/78.3 |

FOREIGN PATENT DOCUMENTS

| | | | |
|---|---|---|---|
| EP | 0492316 A1 * | 7/1992 | ........... C07D 487/04 |
| EP | 2 284 209 | 2/2011 | |
| WO | WO 02/043772 | 6/2002 | |
| WO | WO 03/037384 | 5/2003 | |
| WO | WO 05/028539 | 3/2005 | |
| WO | WO 07/098466 | 8/2007 | |
| WO | WO 09/136572 | 11/2009 | |
| WO | WO 10/019233 | 2/2010 | |
| WO | WO 10/021718 | 2/2010 | |
| WO | WO 11/035065 | 3/2011 | |

OTHER PUBLICATIONS

English Translation of Japanese Notice of Reasons for Rejection in Japanese Patent Application No. 2013-546374 dated Aug. 24, 2015.
Abuchowski, et al., "Cancer Therapy with Chemically Modified Enzymes. I. Antitumor Properties of Polyethylene Glycol-Asparaginase Conjugates," Cancer Biochem. Biophys., vol. 7, pp. 175-186, (1984).
Andresz, et al., Chemische Synthese verzweigter Polysaccharide, 5*), Makromol. Chem., vol. 179, pp. 301-312, (1978).
Bacchi, et al., "Novel Synthetic Polyamines are Effective in the Treatment of Experimental Microsporidiosis, an Opportunistic AIDS-Associated Infection," Antimicrobial Agents and Chemotherapy, vol. 46, No. 1, pp. 55-61, (2002).
Beauchamp, et al., "A New Procedure for the Synthesis of Polyethylene Glycol-Protein Adducts; Effects on Function, Receptor Recognition, and Clearance of Superoxide Dismutase, Lactoferrin, and $\alpha_2$-Macroglobulin," Analytical Biochemistry, vol. 131, pp. 25-33, (1983).
Brinkley, "A Brief Survey of Methods for Preparing Protein Conjugates with Dyes, Haptens, and Cross-Linking Reagents," Bioconjugate Chemistry, vol. 3, pp. 2-13, (1992).
Buckmann, et al., "Functionalization of Poly(ethylene glycol) and Monomethoxy-Poly(ethylene glycol)," Makromol. Chem., vol. 182, pp. 1379-1384, (1981).
Chattopadhyay, et al., "Pemetrexed: biochemical and cellular pharmacology, mechanisms, and clinical applications," Molecular Cancer Therapeutics, vol. 6, No. 2, pp. 404-417, (2007).
Elling, et al., "Immunoaffinity Partitioning: Synthesis and Use of Polyethylene Glycol-Oxirane for Coupling to Bovine Serum Albumin and Monoclonal Antibodies," Biotechnology and Applied Biochemistry, vol. 13, pp. 354-362, (1991).
Goodson, et al., "Site-Directed Pegylation of Recombinant Interleukin-2 at Its Glycosylation Site," Bio/Technology, vol. 8, pp. 345-346, (1990).
Harris, et al., "Synthesis and Characterization of Poly(ethylene Glycol) Derivatives,", Journal of Polymer Science: Polymer Chemistry Edition, vol. 22, pp. 341-352, (1984).

(Continued)

*Primary Examiner* — Sarah Pihonak
*Assistant Examiner* — Jason Deck

(57) ABSTRACT

Among other aspects, provided herein are multi-arm polymeric prodrug conjugates of pemetrexed-based compounds. Methods of preparing such conjugates as well as methods of administering the conjugates are also provided. Upon administration to a patient, release of the pemetrexed-based compound is achieved.

7 Claims, No Drawings

(56) References Cited

OTHER PUBLICATIONS

Joppich, et al., "Peptides Flanked by Two Polymer Chains, 1 Synthesis of Glycyl-L-tryptophylglycine Substituted by Poly(ethylene oxide) at both the Carboxy and the Amino End Groups," Makromol. Chem., vol. 180, pp. 1381-1384, (1979).
Kogan, "The Synthesis of Substituted Methoxy-Poly(EthyleneGlycol) Derivatives Suitable for Selective Protein Modification," Synthetic Communications, vol. 22, No. 16, pp. 2417-2424, (1992).
Olson, et al., "Preparation and Characterization of Poly(ethylene glycol)ylated Human Growth Hormone Antagonist," American Chemical Society, Chapter 12 (Chapter DOI: 10.1021/bk-1997-0680.ch012), pp. 170-181, (1997).
Orban, et al., "Synthesis, characterization and cytostatic effect of new pemetrexed-peptide conjugates," Journal of Peptide Science; 31$^{st}$ European Peptide Symposium (EPS), John Wiley and Sons LTD, GB; Copenhagen, Denmark, vol. 16, No. Suppl. 1, pp. 142-143, (2010), p. 299. Abstract No. 195.
Pitha, et al., "Detergents Linked to Polysaccharides: Preparation and Effects on Membranes and Cells," Eur. J. Biochem., vol. 94, pp. 11-18, (1979).
Romani, et al., "Synthesis of Unsymmetrical Cystine Peptides: Directed Disulfide Pairing with the Sulfenohydrazide Method," Chemistry of Peptides and Proteins, vol. 2, pp. 29-34, (1984).
Sartore, et al., "Enzyme Modification by MPEG with an Amino Acid or Peptide as Spacer Arms,", Applied Biochemistry and Biotechnology, vol. 27, pp. 45-54, (1991).
Sawhney, et al., "Bioerodible Hydrogels Based on Photopolymerized Poly(ethylene glycol)-co-poly($\alpha$-hydroxy acid) Diacrylate Macromers," Macromolecules, vol. 26, pp. 581-587, (1993).
Tondelli, et al., "Poly(Ethylene Glycol) Imidazolyl Formates as Oligomeric Drug-Binding Matrices," Journal of Controlled Release, vol. 1, pp. 251-257, (1985).
Veronese, et al., "Surface Modification of Proteins, Activation of Monomethoxy-Polyethylene Glycols by Phenylchloroformates and Modification of Ribonuclease and Superoxide Dismutase," Applied Biochemistry and Biotechnology, vol. 11, pp. 141-152, (1985).
Woghiren, et al., "Protected Thiol-Polyethylene Glycol: A New Activated Polymer for Reversible Protein Modification," Bioconjugate Chem., vol. 4, pp. 314-318, (1993).
Zalipsky, et al., "Attachment of Drugs to Polyethylene Glycols," Eur. Polym. J., vol. 19, No. 12, pp. 1177-1183, (1983).
PCT International Search Report and Written Opinion corresponding to PCT International Application No. PCT/US2011/066510 dated Feb. 24, 2012.
PCT International Preliminary Report on Patentability corresponding to PCT International Application No. PCT/US2011/066510 dated Jul. 4, 2013.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
Nof Corporation, PEG Derivatives, Phospholipid and Drug Delivery Materials for Pharmaceuticals, 46 pages, Catalogue 2003-1$^{st}$, (Jan. 2003).
Nof Corporation, PEG Derivatives, Phospholipid and Drug Delivery Materials for Pharmaceuticals, 27 pages, Catalogue 2003-2$^{nd}$, (Mar. 2004).
Nof Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Communication pursuant to Art. 94(3) EPC in European pat. appl. No. 11806114.2-1453 dated Jul. 8, 2016.

\* cited by examiner

MULTI-ARM POLYMERIC PRODRUG CONJUGATES OF PEMETREXED-BASED COMPOUNDS

CROSS-REFERENCE TO RELATED APPLICATIONS

This application is a 35 U.S.C. § 371 application of International Application No. PCT/US2011/066510, filed Dec. 21, 2011, designating the United States, which claims the benefit of priority under 35 U.S.C. § 119(e) to U.S. Provisional Patent Application No. 61/425,728, filed Dec. 21, 2010, the disclosures of which are incorporated herein by reference in their entireties.

FIELD

This disclosure relates generally to conjugates of a pemetrexed-based compound conjugated to a multi-arm, water-soluble polymer. The linkage between the pemetrexed-based compound and the multi-arm, water-soluble polymer is releasable, thereby enabling release of the pemetrexed-based compound following administration of the conjugate to a patient. The invention relates to and/or has application(s) in (among others) the fields of drug discovery, pharmacotherapy, physiology, organic chemistry and polymer chemistry.

BACKGROUND

Over the years, numerous methods have been proposed for improving the delivery of biologically active agents, particularly small molecule drugs. Challenges associated with the formulation and delivery of pharmaceutical agents can include poor aqueous solubility of the pharmaceutical agent, toxicity, low bioavailability, instability, and rapid in-vivo degradation. Although many approaches have been devised for improving the delivery of pharmaceutical agents, no single approach is without its drawbacks. For instance, commonly employed drug delivery approaches aimed at solving or at least ameliorating one or more of these challenges include drug encapsulation (such as in a liposome, polymer matrix, or unimolecular micelle), covalent attachment to a water-soluble polymer (i.e., conjugation) such as polyethylene glycol (i.e., PEG or PEGylation), use of gene targeting agents, and the like.

PEGylation has been employed to improve the bioavailability and ease of formulation of small molecule therapeutics having poor aqueous solubilities. For instance, water-soluble polymers such as PEG have been covalently attached to artilinic acid to improve its aqueous solubility. See U.S. Pat. No. 6,461,603. Similarly, PEG has been covalently attached to triazine-based compounds such as trimelamol to improve their solubility in water and enhance their chemical stability. See International Patent Application Publication No. WO 02/043772. Covalent attachment of PEG to bisindolyl maleimides has been employed to improve poor bioavailability of such compounds due to low aqueous solubility. See International Patent Application Publication No. WO 03/037384. Polymer conjugates of non-steroidal anti-inflammatory drugs (NSAIDs) and of opioid antagonists have also been prepared. See U.S. Patent Application Publication Nos. 2007/0025956 and 2006/0105046, respectively. Prodrugs of camptothecin having one or two molecules of camptothecin covalently attached to a linear polyethylene glycol have also been prepared. See U.S. Pat. No. 5,880,131. Prodrugs of irinotecan and docetaxel having (among other things) four molecules of drug covalently attached to a multi-arm polymer have been described in U.S. Pat. No. 7,744,861 and International Patent Application Publication No. WO 10/019,233, respectively.

The antifolate drug, pemetrexed (available under the ALIMTA® brand as the disodium salt from Eli Lilly and Company, Indianapolis Ind.), exhibits inhibition of thymidylate synthase, dihydrofolate reductase and glycinamide ribonucleotide formyltransferase. Approved for treating patients suffering from locally advanced or metastatic nonsquamous non-small cell lung cancer and, in combination with cisplantin, mesothelioma, pemetrexed is also being studied for use in treating patients suffering from other cancers as well.

Use of pemetrexed (like almost all antineoplastic agents) is not without drawbacks. For example, pemetrexed's cytotoxic properties affect both cancerous as well as non-cancerous cells. In particular, pemetrexed is associated gastro-intestinal side effects (e.g., nausea, vomiting and anorexia) with a dose-limiting toxicity of myelosuppression. In addition, relatively frequent dosing of the drug is required given pemetrexed's 3.5 hours half-life with 70-90% of the drug excreted unchanged in the urine.

In order to address at least some of these side effects, the use of additional compounds has been proposed. For example, some have proposed the use of folic acid and a methylmalonic acid lowering agent (e.g., vitamin B12) to reduce the toxicity of pemetrexed. See, for example, U.S. Pat. No. 7,772,209.

It would be desirous, however, if pemetrexed could be modified in such a way so as to achieve one or more of the following (i) reduce peak-to-trough variation (with the potential to reduce dose-limiting toxicities), (ii) accumulate in tumor tissues while still retaining efficacy, and (iii) extend the effective half-life to thereby provide less frequent dosing.

The present invention seeks to address these and/or other needs.

SUMMARY

In one or more embodiments of the invention, conjugates are provided, the conjugates having a structure encompassed by the formula:

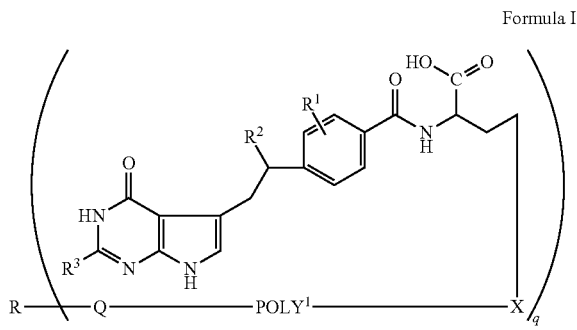

Formula I wherein:

R is a residue of polyol, polythiol or polyamine bearing from 3 to about 50 hydroxyl, thiol or amino groups;

$R^1$ is selected from the group consisting of H, halo (e.g., chloro and fluoro), methyl, methoxy and trifluoromethyl (and is preferably H);

$R^2$ is selected from the group consisting of H and methyl (and is preferably H);

$R^3$ is selected from the group consisting of H, lower alkyl and amino;

Q is a linker (and, in one or more embodiments, a hydrolytically stable linker);

$POLY^1$ is a water-soluble, non-peptidic polymer;

X is spacer moiety that includes a releasable linkage (e.g., a hydrolyzable linkage, an enzymatically degradable linkage, and so forth); and q is a positive integer from 3 to about 50 (e.g., 4), and pharmaceutically acceptable salts and solvates thereof.

In one or more embodiments of the invention, a conjugate-containing composition is provided, the conjugate-containing composition comprising four-arm conjugates, wherein at least 80% of the four-arm conjugates in the composition have a structure encompassed by the formula, Formula I

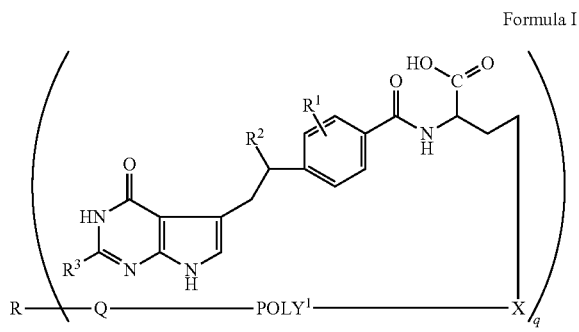

wherein:

R is a residue of polyol, polythiol or polyamine bearing from 3 to about 50 hydroxyl, thiol or amino groups;

$R^1$ is selected from the group consisting of H, halo (e.g., chloro and fluoro), methyl, methoxy and trifluoromethyl (and is preferably H);

$R^2$ is selected from the group consisting of H and methyl (and is preferably H);

$R^3$ is selected from the group consisting of H, lower alkyl and amino;

Q is a linker (and, in one or more embodiments, a hydrolytically stable linker);

$POLY^1$ is a water-soluble, non-peptidic polymer;

X is spacer moiety that includes a releasable linkage (e.g., a hydrolyzable linkage, an enzymatically degradable linkage, and so forth); and q is a positive integer from 3 to about 50 (e.g., 4), and pharmaceutically acceptable salts and solvates thereof.

In one or more embodiments of the invention, conjugates are provided, the conjugates having a structure encompassed by the formula:

Formula Ia

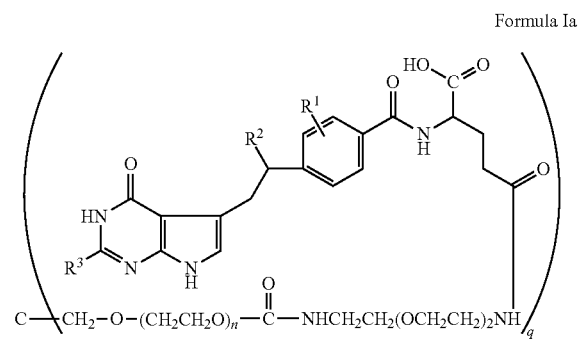

wherein:

$R^1$ is selected from the group consisting of H, halo (e.g., chloro and fluoro), methyl, methoxy and trifluoromethyl (and is preferably H);

$R^2$ is selected from the group consisting of H and methyl (and is preferably H);

$R^3$ is selected from the group consisting of H, lower alkyl and amino;

each n is a positive integer from 10 to about 400; and q is a positive integer from 3 to about 50 (e.g., 4), and pharmaceutically acceptable salts and solvates thereof.

In one or more embodiments of the invention, conjugates are provided, the conjugates having a structure encompassed by the formula:

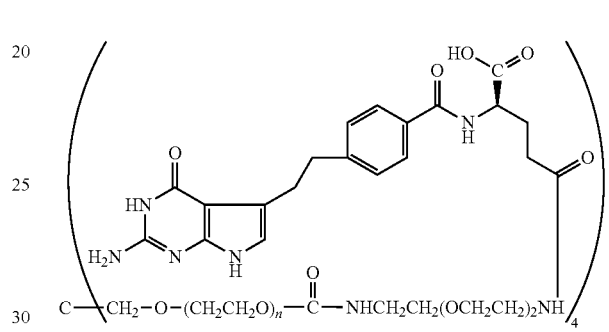

wherein each n is a positive integer from 10 to about 400, and pharmaceutically acceptable salts and solvates thereof.

In one or more embodiments of the invention, conjugates are provided, the conjugates having a structure encompassed by the formula:

Formula Ib

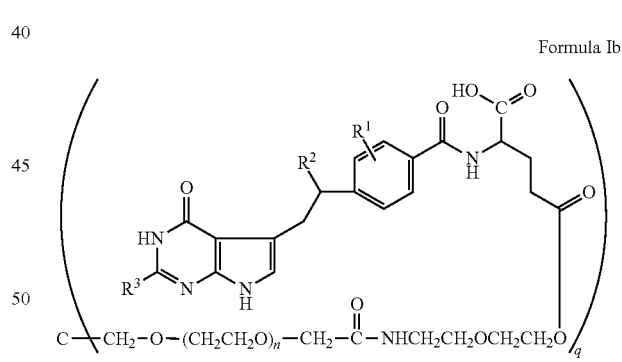

wherein:

$R^1$ is selected from the group consisting of H, halo (e.g., chloro and fluoro), methyl, methoxy and trifluoromethyl (and is preferably H);

$R^2$ is selected from the group consisting of H and methyl (and is preferably H);

$R^3$ is selected from the group consisting of H, lower alkyl and amino;

each n is a positive integer from 10 to about 400; and q is a positive integer from 3 to about 50 (e.g., 4), and pharmaceutically acceptable salts and solvates thereof.

In one or more embodiments of the invention, conjugates are provided, the conjugates having a structure encompassed by the following formula:

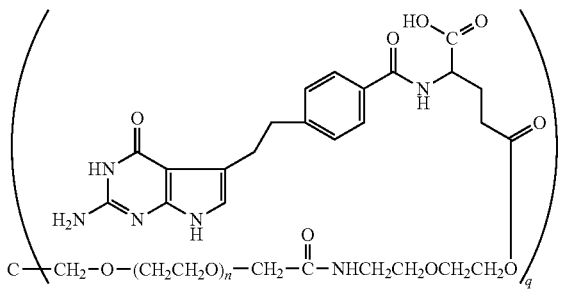

wherein each n is a positive integer from 10 to about 400, and pharmaceutically acceptable salts and solvates thereof.

In one or more embodiments of the invention, conjugates are provided, the conjugates having a structure encompassed by the formula:

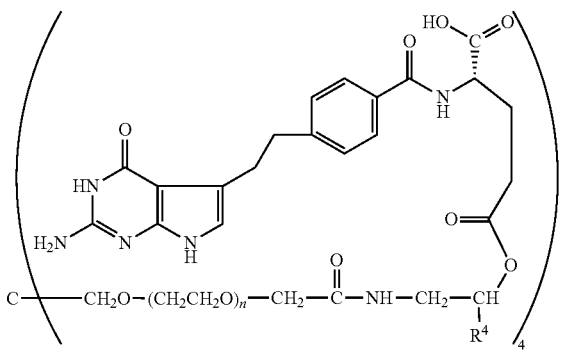

wherein:

$R^4$ is selected from the group consisting of H, $CH_3$, $CH(CH_3)_2$, $CH_2CH(CH_3)_2$ and $C(H)(CH_3)CH_2CH_3$;

each n is a positive integer from 10 to about 400;

and pharmaceutically acceptable salts and solvates thereof.

In one or more embodiments of the invention, a pharmaceutical composition is provided, the pharmaceutical composition comprising a conjugate as described herein and a pharmaceutically acceptable carrier.

In one or more embodiments of the invention, a method is provided, the method comprising administering a conjugate as described herein (preferably in a pharmaceutical composition containing a pharmaceutically acceptable amount of the conjugate) to an individual.

In one or more embodiments of the invention, a method is provided, the method comprising a contacting a multi-aim water-soluble, non-peptidic polymer structure having "q" polymer arms, each individual polymer arm bearing a nucleophile at its terminus, with "q" moles or greater of a compound having the following structure:

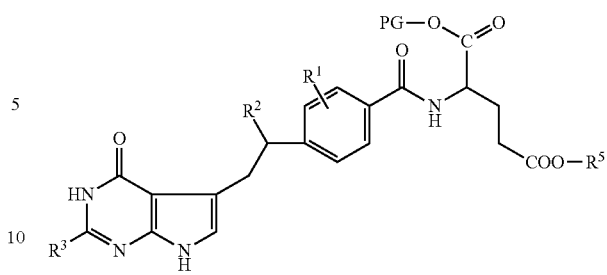

wherein:

$R^1$ is selected from the group consisting of H, halo (e.g., chloro and fluoro), methyl, methoxy and trifluoromethyl (and is preferably H);

$R^2$ is selected from the group consisting of H and methyl (and is preferably H);

$R^3$ is selected from the group consisting of H, lower alkyl and amino;

$R^5$ is H or an activating group for a carboxylic acid (e.g., N-succinimidyl); and PG is a carboxylic acid protecting group, which method further comprises, following the contacting step, the optional step of deprotecting the carboxylic acid protecting group.

Additional embodiments of the present conjugates, compositions, methods, and the like will be apparent from the description that follows. Additional aspects and advantages of the present invention are set forth in the following description and claims, particularly when considered in conjunction with the accompanying examples and drawings.

DETAILED DESCRIPTION

Various aspects of the invention now will be described more fully hereinafter. Such aspects may, however, be embodied in many different forms and should not be construed as limited to the embodiments set forth herein; rather, these embodiments are provided so that this disclosure will be thorough and complete, and will fully convey the scope of the invention to those skilled in the art.

Definitions

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

A "functional group" is a group that may be used, under normal conditions of organic synthesis, to form a covalent linkage between the entity to which it is attached and another entity, which typically bears a further functional group. The functional group generally includes multiple bond(s) and/or heteroatom(s). Preferred functional groups for use in the polymers of the invention are described below.

The term "reactive" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive", with reference to a functional group present on a molecule in a reaction mixture, indicates that the group remains largely intact under conditions effective to produce a desired reaction in the reaction mixture.

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include, for example, imidazolyl esters, and benzotriazole esters, and imide esters, such as N-hydroxysuccinimidyl (NHS) esters. An activated derivative may be formed in situ by reaction of a carboxylic acid with one of various reagents, e.g. benzotriazol-1-yloxy tripyrrolidinophosphonium hexafluorophosphate (PyBOP), preferably used in combination with 1-hydroxy benzotriazole (HOBT) or 1-hydroxy-7-azabenzotriazole (HOAT); O-(7-azabenzotriazol-1-yl)-N,N,N',N'-tetramethyluronium hexafluorophosphate (HATU); or bis(2-oxo-3-oxazolidinyl) phosphinic chloride (BOP—Cl).

A "chemical equivalent" of a functional group is one that possesses essentially the same type of reactivity as the functional group. For instance, one functional group that undergoes an SN2 reaction is considered, to be a functional equivalent of another such functional group.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups that may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, representative protecting groups include carbamates (such as tert-butoxycarbonyl) and amides; for hydroxyl groups, representative protecting groups include ethers and esters; for thiol groups, representative protecting groups include thioethers and thioesters; for carbonyl groups, representative protecting groups include acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and in P. J. Kocienski, *Protecting Groups*, Third Ed., Thieme Chemistry, 2003, and references cited therein.

A functional group in "protected form" refers to a functional group bearing a protecting group. As used herein, the term "functional group" or any synonym thereof is meant to encompass protected forms thereof.

"PEG" or "poly(ethylene glycol)" as used herein, is meant to encompass any water-soluble poly(ethylene oxide). Typically, PEGs for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation, or, e.g., the identity of adjacent functional groups. The variable (n) typically ranges from 3 to about 3000, and the terminal groups and architecture of the overall PEG may vary. When PEG or a conjugate comprising a PEG segment further comprises a spacer or a linker as in Formula I (when POLY is a PEG"), the atoms comprising the spacer (X) and linker (Q), when covalently attached to a PEG segment, do not result in formation of (i) an oxygen-oxygen bond (—O—O—, a peroxide linkage), or (ii) a nitrogen-oxygen bond (N—O, O—N). PEGs for use in the invention include PEGs having a variety of molecular weights, structures or geometries to be described in greater detail below.

"Water-soluble," in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

"Non-naturally occurring" with respect to a polymer means a polymer that in its entirety is not found in nature. A non-naturally occurring polymer may however contain one or more subunits or segments of subunits that are naturally occurring, so long as the overall polymer structure is not found in nature.

"Molecular mass" in the context of a water-soluble polymer such as PEG, refers to the nominal average molecular mass of a polymer, typically determined by size exclusion chromatography, light scattering techniques, or intrinsic viscosity determination in water or organic solvents. Molecular weight in the context of a water-soluble polymer, such as PEG, can be expressed as either a number-average molecular weight or a weight-average molecular weight. Unless otherwise indicated, all references to molecular weight herein refer to the number-average molecular weight. Both molecular weight determinations, number-average and weight-average, can be measured using gel permeation chromatographic techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 1.2, less than about 1.15, less than about 1.10, less than about 1.05, and less than about 1.03. As used herein, references will at times be made to a single water-soluble polymer having either a weight-average molecular weight or number-average molecular weight; such references will be understood to mean that the single-water soluble polymer was obtained from a composition of water-soluble polymers having the stated molecular weight.

The terms "spacer moiety" and "linker" are used herein to refer to an atom or a collection of atoms used to link interconnecting moieties, such pemetrexed and a water-soluble, non-peptidic polymer, POLY$^1$. A "spacer moiety" and "linker" may be hydrolytically stable or may include a releasable linkage (e.g., a physiologically hydrolyzable linkage, an enzymatically degradable linkage, or another linkage that cleaves in vivo).

A "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Illustrative hydrolytically unstable linkages include carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes. Such a linkage requires the action of one or more enzymes to effect degradation.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multi-armed" in reference to the geometry or overall structure of a polymer refers to polymer having 3 or more polymer-containing "arms" connected to a "core" molecule or structure. Thus, a multi-armed polymer may possess 3 polymer arms, 4 polymer arms, 5 polymer arms, 6 polymer arms, 7 polymer arms, 8 polymer arms or more, depending upon its configuration and core structure. One particular type of highly branched polymer is a dendritic polymer or dendrimer, that, for the purposes of the invention, is considered to possess a structure distinct from that of a multi-armed polymer. That is to say, a multi-armed polymer as referred to herein explicitly excludes dendrimers. Additionally, a multi-armed polymer as provided herein possesses a non-crosslinked core.

A "dendrimer" is a globular, size monodisperse polymer in which all bonds emerge radially from a central focal point or core with a regular branching pattern and with repeat units that each contribute a branch point. Dendrimers are typically formed using a nano-scale, multistep fabrication process. Each step results in a new "generation" that has two or more times the complexity of the previous generation. Dendrimers exhibit certain dendritic state properties such as core encapsulation, making them unique from other types of polymers.

"Branch point" refers to a bifurcation point comprising one or more atoms at which a polymer splits or branches from a linear structure into one or more additional polymer aims. A multi-arm polymer may have one branch point or multiple branch points, so long as the branches are not regular repeats resulting in a dendrimer.

"Substantially" or "essentially" means nearly totally or completely, for instance, 95% or greater of some given quantity.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, isopropyl, n-butyl, n-pentyl, 2-methyl-1-butyl, 3-pentyl, 3-methyl-3-pentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

As used herein, "alkenyl" refers to a branched or unbranched hydrocarbon group of 1 to 15 atoms in length, containing at least one double bond, such as ethenyl (vinyl), 2-propen-1-yl (allyl), isopropenyl, 3-buten-1-yl, and the like.

The term "alkynyl" as used herein refers to a branched or unbranched hydrocarbon group of 2 to 15 atoms in length, containing at least one triple bond, ethynyl, 1-propynyl, 3-butyn-1-yl, 1-octyn-1-yl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein includes any agent, drug, compound, and the like which provides some pharmacologic, often beneficial, effect that can be demonstrated in vivo or in vitro. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in a target tissue or site in the body. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multi-functional" in the context of a polymer of the invention means a polymer having 3 or more functional groups, where the functional groups may be the same or different, and are typically present on the polymer termini. Multi-functional polymers of the invention will typically contain from about 3-100 functional groups, or from 3-50 functional groups, or from 3-25 functional groups, or from 3-15 functional groups, or from 3 to 10 functional groups, i.e., contains 3, 4, 5, 6, 7, 8, 9 or 10 functional groups. Typically, in reference to a polymer precursor used to prepare a polymer conjugate of the invention, the polymer possesses 3 or more polymer arms having at the terminus of each arm a functional group suitable for coupling to an active agent moiety via a hydrolyzable ester linkage. Typically, such functional groups are the same.

A basic or acidic reactant described herein includes neutral, charged, and any corresponding salt forms thereof.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer may include a minor number of peptide linkages spaced along the repeat monomer subunits, such as, for example, no more than about 1 peptide linkage per about 50 monomer units.

The terms "subject," "individual" or "patient" are used interchangeably herein and refer to a vertebrate, preferably a mammal. Mammals include, but are not limited to, murines, rodents, simians, humans, farm animals, sport animals and pets. Such subjects are typically suffering from or prone to a condition that can be prevented or treated by administration of a polymer of the invention, typically but not necessarily in the form of a polymer-active agent conjugate as described herein.

"Treatment" or "treating" of a particular condition includes: (1) preventing such a condition, i.e., causing the condition not to develop, or to occur with less intensity or to a lesser degree in a subject that may be exposed to or predisposed to the condition but does not yet experience or display the condition; and (2) inhibiting the condition, i.e., arresting the development or reversing the condition.

"Optional" or "optionally" means that the subsequently described circumstance may or may not occur, so that the description includes instances where the circumstance occurs and instances where it does not.

A "residue" refers to a portion of compound remaining or present following a chemical reaction (whether a synthetic chemical reaction or following compound releasing-chemical reaction). For example, a polyol that is used to form a multi-aim polymer will have a "residue" of that polyol present in the multi-arm polymer.

A "polyol" is an alcohol containing more than two hydroxyl groups, where the prefix "poly" in this instance refers to a plurality of a certain feature rather than to a polymeric structure. Similarly, a polythiol is a thiol containing more than two thiol (—SH) groups, and a polyamine is an amine containing more than two amino groups.

As previously indicated, one or more embodiments of the invention relate to conjugates having a structure encompassed by Formula I. The conjugates of the invention are both prodrugs (given the presence of a spacer moiety that includes a releaseable linkage) and "multi-armed." Thus, upon administration to an individual, the prodrug releases in vivo a compound lacking attachment to the water-soluble, non-peptidic polymer via in vivo cleavage. For example, in vivo cleavage of an ester may occur with or without the benefit of an esterase. In an additional example, in vivo cleavage of an amide may occur with the benefit of, for example, a γ-glutamyl hydrolase. Because the conjugates are multi-armed, release occurs multiple times, thereby delivering following administration several moles of released compound for each mole of starting conjugate.

Thus, an exemplary conjugates of the invention have a structure encompassed by the formula:

Formula I

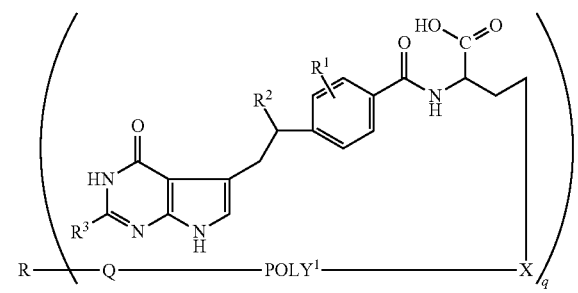

wherein:

R is a residue of polyol, polythiol or polyamine bearing from 3 to about 50 hydroxyl, thiol or amino groups;

$R^1$ is selected from the group consisting of H, halo (e.g., chloro and fluoro), methyl, methoxy and trifluoromethyl (and is preferably H);

$R^2$ is selected from the group consisting of H and methyl (and is preferably H);

$R^3$ is selected from the group consisting of H, lower alkyl and amino;

Q is a linker (and, in one or more embodiments, a hydrolytically stable linker);

$POLY^1$ is a water-soluble, non-peptidic polymer;

X is spacer moiety that includes a releasable linkage (e.g., a hydrolyzable linkage, an enzymatically degradable linkage, and so forth); and q is a positive integer from 3 to about 50 (e.g., 4), and pharmaceutically acceptable salts and solvates thereof.

It will be appreciated that the oxo forms of the heterocyclic rings described herein are tautomeric equivalents of the corresponding $R^3$-substituted pyrrolo[2,3-d]pyrimidines.

As contemplated by the above structure, the conjugate has "q" number of arms, i.e., from 3 to about 50. An exemplary number of arms includes 3, 4, 5, 6, 7, 9, and 10. In one or more embodiments, the conjugates of the invention are prepared from multi-armed polymer reagents, which, in turn, are prepared from multi-arm polymers based on a multi-arm core molecule.

For example, in one approach, a multi-arm polymer can be prepared from a multi-arm core molecule by effectively "growing" a polymer onto each terminus of a multi-arm core molecule. By way of non-limiting example, it is possible to synthesize a polymer arm onto a polyol (e.g., pentaerythritol, diglycerol, etc.) via an ethoxylation reaction. In another exemplary approach, a multi-arm polymer can be prepared from a multi-arm in core molecule by attaching a water-soluble, non-peptidic polymer onto each terminus of a multi-arm core molecule. The principles of both approaches are described in the literature and in, for example, U.S. Pat. No. 7,026,440. The invention, however, is not limited with regard to the specific approach taken, so long as the conjugate is encompassed by one or more of the structures provided herein.

The Residue of the Polyol, Polythiol, or Polyamine, "R"

In one or more embodiments, the residue of the polyol, polythiol or polyamine, "R," is an organic radical-containing moiety. The polyol, polythiol or polymamine from which "R" is derived possesses from about 3 to about 150 carbon atoms (e.g., from about 3 to about 50 carbon atoms, such as 3, 4, 5, 6, 7, 8, 9, and 10). The residue may contain one more heteroatoms (e.g., O, S, or N). In addition, the residue may be linear. In some instances, the residue may be cyclic.

As previously indicated, the residue of the polyol, polythiol or polyamine, "R," that forms the basis of the branching for the multi-armed conjugates provided herein, originated from a corresponding polyol, polythiol or polyamine (prior to be incorporated into the multi-arm structures containing a water-soluble, non-peptidic polymer). In one or more embodiments, the corresponding polyol, polythiol, or a polyamine bears at least three hydroxyl, thiol, or amino groups, respectively, available for polymer attachment. A preferred polyol is a molecule comprising three or more hydroxyl groups. A preferred polythiol is a molecule that comprises three or more thiol groups. A preferred polyamine is a molecule comprising three or more amino groups.

In one or more embodiments, the polyol, polyamine or polythiol will typically contain 3 to about 25 hydroxyl, or amino groups or thiol groups, respectively, such as from 3 to about 10 (i.e., 3, 4, 5, 6, 7, 8, 9, 10) hydroxyl, amino groups or thiol groups, respectively, preferably from 3 to about 8 (i.e., 3, 4, 5, 6, 7, or 8) hydroxyl, amino groups or thiol groups, respectively. In one or more embodiments, the number of atoms between each hydroxyl, thiol, or amino group will vary, although lengths of from about 1 to about 20 (e.g., from 1 to about 5) intervening atoms, such as carbon atoms, between each hydroxyl, thiol or amino group, are exemplary. In referring to intervening core atoms and lengths, —CH$_2$— is considered as having a length of one intervening atom, —CH$_2$CH$_2$— is considered as having a length of two atoms, and so forth.

Exemplary polyols and polyamines (for which corresponding residues could be present in the conjugates provided herein) have a (Radical)-(OH)$_q$ and (Radical)-(NH$_2$)$_q$ structure, respectively, where (Radical) corresponds to an organic-containing radical and q is a positive integer from 3 to about 50. Note that in Formula I, the variable "Q," when taken together with R, typically represents a residue of the core organic radical as described herein. That is to say, when describing polyols, polythiols and polymer amines, particularly by name, these molecules are being referenced in their form prior to incorporation into a water-soluble polymer-containing structure. So, for example, a conjugate of Formula I wherein R is a residue of the polyol, pentaerythritol [C(CH$_2$OH)$_4$], the residue "R" includes carbon (i.e., "C,") and, together with "Q," represents "C(CH$_2$O—)$_4$."

Illustrative polyols include aliphatic polyols having from 1 to 10 carbon atoms and from 3 to 10 hydroxyl groups, including for example, trihydroxyalkanes, tetrahydroxyalkanes, polyhydroxy alkyl ethers, polyhydroxyalkyl polyethers, and the like. Cycloaliphatic polyols include straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional examples of aliphatic polyols include derivatives of glucose, ribose, mannose, galactose, and related stereoisomers. Aromatic polyols may also be used, such as 1,1,1-tris(4'-hydroxyphenyl) alkanes, such as 1,1,1-tris(4-hydroxyphenyl)ethane, 2,6-bis(hydroxyalkyl)cresols, and the like. Other core polyols that may be used include polyhydroxycrown ethers, cyclodextrins, dextrins and other carbohydrates (e.g., monosaccharides, oligosaccharides, and polysaccharides, starches and amylase).

Exemplary polyols include glycerol, trimethylolpropane, pentaerythritol, dipentaerythritol, tripentaerythritol and ethoxylated forms of glycerol. Also, preferred are reducing sugars such as sorbitol and glycerol oligomers, such as diglycerol, triglycerol, hexaglycerol and the like. A 21-arm polymer can be synthesized using hydroxypropyl-β-cyclodextrin, which has 21 available hydroxyl groups. Additionally, a polyglycerol having an average of 24 hydroxyl groups is also included as an exemplary polyol.

Exemplary polyamines include aliphatic polyamines such as diethylene triamine, N,N',N"-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methylamine, and N,N-dimethyl-dipropylene-triamine. Naturally occurring polyamines that can be used in the present invention include putrescine, spermidine, and spermine. Numerous suitable pentamines, tetramines, oligoamines, and pentamidine analogs suitable for use in the present invention are described in Bacchi et al. (2002) *Antimicrobial Agents and Chemotherapy*, 46(1):55-61, which is incorporated by reference herein.

Provided below are illustrative structures corresponding to residues of polyols [although each structure is depicted with the oxygen atom ("O") derived from the corresponding hydroxyl group, each "O" can be substituted with sulfur ("S") or NH to depict the corresponding residue of a polythiol or polyamine, respectively). Note that the residues shown below would be understood in terms of compounds of Formula I as corresponding to "R" and "Q." In any event, conjugates based on any of the illustrative structures set forth below are included as part of the invention.

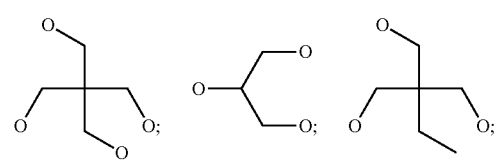

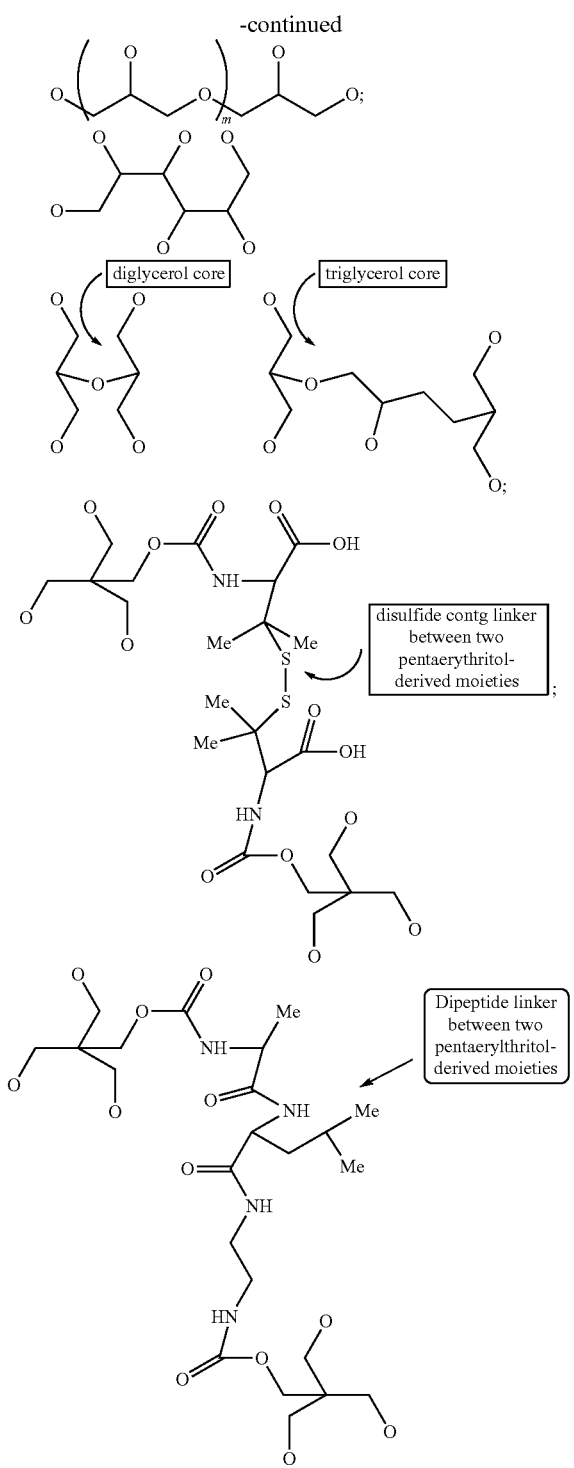

and
wherein m is a positive integer from 0-40 [preferably 0-10, e.g., 0-5 (i.e., 0, 1, 2, 3, 4, 5)].

Water-soluble, non-peptidic-containing multi-arm polymers (used as, for example, multi-arm polymeric reagents to prepare conjugates encompassed by Formula I) based on the above-described polyols, polythiols and polyamines and others are described in WO 2007/098466, WO 2010/019233 and U.S. Pat. No. 7,744,861. These references and others describe methods for preparing such multi-arm polymers. In addition, some multi-arm polymers are available commercially from, for example, Creative PEGWorks (Winston Salem, N.C. USA), SunBio PEG-Shop (SunBio USA, Orinda, Calif.), JenKem Technology USA (Allen, Tex.), and NOF America Corporation (White Plains, N.Y.).

The Linker, "Q"

The linker, Q, serves to connect the residue of the polyol, polythiol or polyamine bearing at from 3 to about 50 hydroxyl, thiol or amino groups, "R," to each water-soluble, non-peptidic polymer, POLY$^1$, in conjugates according to Formula I. In this regard, the invention is not limited with respect to the specific linker used. In one or more embodiments, the linker between the residue, "R," and the water-soluble, non-peptidic polymer, POLY$^1$, is a hydrolytically stable linker.

In one or more embodiments of the invention, the linker, Q, is influenced by the approach used to form the multi-arm polymer employed in preparing the conjugates of the invention. For example, if a water-soluble, non-peptidic polymer bearing a functional group reactive to a hydroxyl, thiol or amine is reacted with a polyol, polythiol or polyamine, respectively, the linker, Q, may include one or more atoms incorporating the bond formed between the termini of the polyol, polythiol or polamine and the beginning of the repeating monomers of the water-soluble, non-peptidic polymer, POLY$^1$. Illustrative linking chemistries in this regard (along with the resulting linkers) are described in the literature and in, for example, Wong (1991) "*Chemistry of Protein Conjugation and Crosslinking*", CRC Press, Boca Raton, Fla., and Brinkley (1992) *Bioconjug. Chem.* 3:2013.

In one or more embodiments of conjugates of Formula I, Q contains at least one heteroatom such as O, or S, or NH, where the atom proximal to R in Q, when taken together with R, typically represents a residue of an organic radical-containing core of the polyol, polythiol or polyamine. Generally, the linker, Q, contains from 1 to about 10 atoms (e.g., from 1 to about 5 atoms). The linker, Q, typically contains a number of atoms selected from the group consisting of: 1, 2, 3, 4, 5, 6, 7, 8, 9, or 10. Illustrative Qs include —O—, —S—, —NH—, —NH—C(O)— and —C(O)—NH—.

The Water-soluble, Non-peptidic Polymer, POLY$^1$

The conjugates of the invention include several water-soluble, non-peptidic polymers as part of the overall structure. With respect to conjugates, each the water-soluble, non-peptidic polymer in the conjugate (e.g., POLY$^1$ in connection with compounds encompassed by Formula I) is independently selected, although preferably, each water-soluble, non-peptidic polymer is the same polymer type. That is, for example, each POLY$^1$ in the multi-armed conjugate is the same.

Any of a variety of water-soluble, non-peptidic polymers that are non-peptidic and water-soluble can be used in the multi-atm conjugates and the invention is not limited in this regard. Examples of water-soluble, non-peptidic polymers include poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), polymers described in U.S. Pat. No. 5,629,384, and copolymers, terpolymers, and mixtures of any one or more of the above.

When the water-soluble, non-peptidic polymer, e.g., POLY$^1$, is PEG, its structure typically comprises —(CH$_2$CH$_2$O)$_n$— (wherein the terminal ethylene is covalently attached to "Q" and the terminal oxygen is attached to "X," with respect to conjugates encompassed by Formula I), where n may range from about 5 to about 400, preferably from about 10 to about 350, or from about 20 to about 300.

Exemplary molecular weights for the water-soluble, non-peptidic polymer (e.g., POLY$^1$) include about 200, about 250, about 300, about 400, about 500, about 600, about 700, about 800, about 900, about 1,000, about 1,500, about 2,000, about 3,000, about 4,000, about 5,000, about 6,000, about 7,000, about 7,500, about 8,000, about 9,000, about 10,000, about 12,000, about 15,000, about 17,500, about 18,000, about 19,000 and about 20,000 Daltons. In terms of the molecular weight of the multi-armed polymer, exemplary molecular weights include: about 800, about 1,000, about 1,200, about 1,600, about 2,000, about 2,400, about 2,800, about 3,200, about 3,600, about 4,000, about 5,000, about 6,000, about 8,000, about 10,000, about 12,000, about 15,000, about 16,000, about 20,000, about 24,000, about 25,000, about 28,000, about 30,000, about 32,000, about 36,000, about 40,000, about 45,000, about 48,000, about 50,000, about 60,000, about 80,000 and about 100,000 Daltons. With respect to molecular weight ranges for the multi-armed polymer, exemplary ranges include: from about 800 to about 80,000 Daltons; from about 900 to about 70,000 Daltons; From about 1,000 to about 40,000 Daltons; from 5,000 to about 30,000 Daltons; and from about 20,000 to about 80,000 Daltons.

The Spacer Moiety, X

The spacer moiety, X, serves to connect the water-soluble, non-peptidic polymer (e.g., POLY$^1$ in conjugates according to Formula I) to the pemetrexed-based compound. Included as part of the spacer moiety is a hydrolyzable linkage (generally an ester linkage). In this regard, the invention is not limited with respect to the specific linker used, so long as the overall linkage includes as a part of the linkage, a hydrolyzable linkage.

As part of the spacer moiety, X, the portions of the spacer moiety may include one or more components selected from the group consisting of —O—, —S—, —NH—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —NH—C(O)—CH$_2$—CH$_2$—CH$_2$—, —CH$_2$—NH—C(O)—CH$_2$—CH$_2$—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, and —NH—C(O)—NH—(CH$_2$)$_{1-6}$—NH—C(O)—. For purposes of the present disclosure, however, a series of atoms is not a spacer moiety when the series of atoms is immediately adjacent to a water-soluble polymer and the series of atoms is but another monomer, such that the proposed spacer moiety would represent a mere extension of the polymer chain.

In one or more embodiments of the invention, the spacer moiety, X, may include a cycloalkylene group, e.g. 1,3- or 1,4-cyclohexylene.

In one or more embodiments of the invention, the spacer moiety, X, has an atom length of from about 1 atom to about 50 atoms, or more preferably from about 1 atom to about 25 atoms, or even more preferably from about 1 atom to about 10 atoms. Typically, the spacer moiety is of an atom length selected from the group consisting of 1, 2, 3, 4, 5, 6, 7, 8, 9 and 10. When considering atom chain length, only atoms contributing to the overall distance are considered. For example, a spacer having the structure, —C̲H̲$_2$—C̲(O)—N̲H̲—C̲H̲$_2$C̲H̲$_2$O̲—C̲H̲$_2$C̲H̲$_2$O̲—C̲(O)—O̲— has a chain length of 11 atoms, since substituents are not considered to contribute to the length of the spacer.

In one or more embodiments of the invention, the spacer moiety, X, is the spacer moiety, Y, optionally further attached to "Z" (i.e., Y—Z), in the latter case where Y is a spacer moiety covalently attached to Z, a hydrolytically degradable linkage. In certain embodiments, Z itself may not constitute a hydrolytically degradable linkage, however, when taken together with Y, or at least a portion of Y, forms a linkage that is hydrolytically degradable.

In one or more embodiments of the invention, when the spacer moiety, X, includes "Y," Y will have the structure: —(CR$_x$R$_y$)$_a$—K$_w$—(CR$_x$R$_y$)$_b$—(CH$_2$CH$_2$O)$_c$—(CR$_x$R$_y$)$_d$—K$_z$—, wherein each R$_x$ and R$_y$, in each occurrence, is independently H or an organic radical selected from the group consisting of alkyl, substituted alkyl, alkenyl, substituted alkenyl, alkynyl, substituted alkynyl, aryl, and substituted aryl, a ranges from 0 to 12 (i.e., can be 0, 1, 2, 3, 4, 5, 6, 7, 8, 9, 10, 11, or 12), b ranges from 0 to 12 (i.e., can be 0, 1, 2, 3, 4, 5, 6, 7, 8, 9, 10, 11, or 12), each of K$_w$ and K$_z$ is independently selected from —NH—, —C(O)—, —C(O)NH—, —NH—C(O)—, —O—, —S—, O—C(O)—, C(O)—O—, —O—C(O)—O—, O—C(O)—NH—, —NH—C(O)—O—, c ranges from 0 to 25, and Z is selected from C(O)—O—, O—C(O)—O—, —O—C(O)—NH— and —NH—C(O)—O—, d ranges from 0 to 12 (i.e., can be 0, 1, 2, 3, 4, 5, 6, 7, 8, 9, 10, 11, or 12). The particular structure of K$_w$, K$_z$ and of Z will depend upon the values of each of a, b, c, and d such that none of the following linkages result in the overall structure of the spacer moiety, X: —O—O—, NH—O—, —NH—NH—.

In one or more embodiments of the invention, when the spacer moiety, X, is Y—Z, Y will have the structure: —(CR$_x$R$_y$)$_a$—K$_w$—(CR$_x$R$_y$)$_b$—(CH$_2$CH$_2$O)$_c$—(CR$_x$R$_y$)$_d$—K$_z$—, where the variables R$_x$, R$_y$, K$_w$, K$_z$, a, b, c and d have the values described in the previous paragraph.

In one or more embodiments of the invention, $R_x$ and $R_y$ (as set forth in each of the two preceding paragraphs) is, in each occurrence, independently H or lower alkyl. In one or more embodiments of the invention, $R_x$ and $R_y$ are, in each occurrence, H. In yet another embodiment, "a" ranges from 0 to 5, i.e., is selected from 0, 1, 2, 3, 4, or 5. In yet another embodiment, b ranges from 0 to 5, i.e., is selected from 0, 1, 2, 3, 4, or 5. In yet another embodiment, c ranges from 0 to 10. In yet another embodiment, "d" ranges from 0 to 5, i.e., is selected from 0, 1, 2, 3, 4, or 5. In yet another embodiment, $K_w$ is —C(O)—NH.

In one or more embodiments, the spacer moiety, X, can also include one or more amino acid residues. In such embodiments, exemplary amino acid residues are residues from the amino acids selected from the group consisting of: alanine, valine, leucine, isoleucine, glycine, threonine, serine, cysteine, methionine, tyrosine, phenylalanine, tryptophan, aspartic acid, glutamic acid, lysine, arginine, histidine, proline, and non-naturally occurring amino acids.

The Pemetrexed-Based Compounds

The multi-arm polymer conjugates described herein include a reside of a pemetrexed-based compound having the following structure:

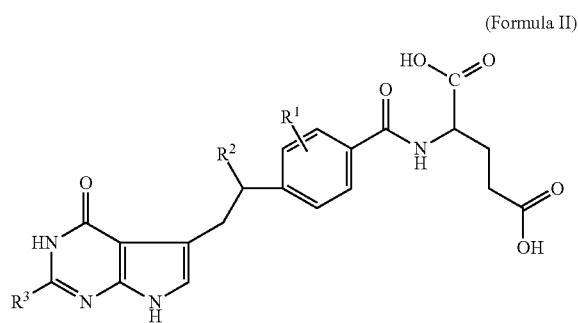

(Formula II)

wherein:

$R^1$ is selected from the group consisting of H, halo (e.g., chloro and fluoro), methyl, methoxy and trifluoromethyl (and is preferably H);

$R^2$ is selected from the group consisting of H and methyl (and is preferably H); and $R^3$ is selected from the group consisting of H, lower alkyl and amino.

Certain exemplary forms of the pemetrexed-based compounds (including their syntheses) are described in U.S. Pat. No. 5,344,932. Other forms of the pemetrexed-based compounds of Formula II can be prepared by one of ordinary skill in the by reference to the disclosure provided herein in view of U.S. Pat. No. 5,344,932 and other literature.

Method of Preparing the Conjugates of the Invention

The conjugates of the invention can be prepared using conventional synthetic approaches of organic chemistry and the invention is not limited with respect to the manner in which the conjugates are made.

In one approach for preparing conjugates of the invention, a multi-arm polymer reagent (which can be obtained from commercially available sources, such as Creative PEG-Works, SunBio PEG-Shop, JenKem Technology USA, and NOF America Corporation, or prepared in accordance with descriptions provided in the literature) is contacted, under conjugation conditions, with an excess (typically at least a molar excess of the number of "q" polymer arms of the reagent) of the pemetrexed-based compound. Conjugation conditions are those conditions of temperature, pH, time, solvent, and so forth that allow for covalent attachment between a reactive group of the reagent to a functional group of the taxoid-based compound. Exemplary conjugation conditions between a given polymer reagent bearing a reactive group and a corresponding functional group of a taxoid-based compound will be known to one of ordinary skill in the art in view of the disclosure provided herein. See, for example, Poly(ethylene glycol) Chemistry and Biological Applications, American Chemical Society, Washington, D.C. (1997).

A multi-armed polymer reagent suitable for use in connection with conjugation conditions will typically have reactive groups selected from the group consisting of: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). As provided in these references, exemplary conjugation conditions (including conditions of temperature, pH, time and solvent) for a given reactive group of a polymer reagent are disclosed.

In one or more embodiments, the pemetrexed-based compound described herein may include one or more protected carboxylic acid groups. With respect to preparing the conjugates, in one approach, the protecting group can be removed after conjugating the pemetrexed-based compound with a polymer reagent.

Following the initial conjugation, compositions containing the conjugates of Formula I can be purified. Methods of purification and isolation include precipitation followed by filtration and drying, as well as chromatography. Suitable chromatographic methods include gel filtration chromatography, ion exchange chromatography, and flash chromatography.

Salts of the Conjugates

The conjugates may be used in their base form. In addition, the conjugates may be used in the form corresponding to a pharmaceutically acceptable salt of the conjugate, and any reference to the conjugates of the invention herein is intended to include pharmaceutically acceptable salts. If used, a salt of a compound as described herein should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the compound with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulfonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

Compositions of Conjugates of the Invention

In certain instances, due to incomplete conversions, less than 100% yields, and other unavoidable complications routinely encountered during chemical syntheses, exemplary compositions of four-arm conjugates are those wherein at least 80% of the four-arm conjugates in the composition have a structure encompassed by the formula,

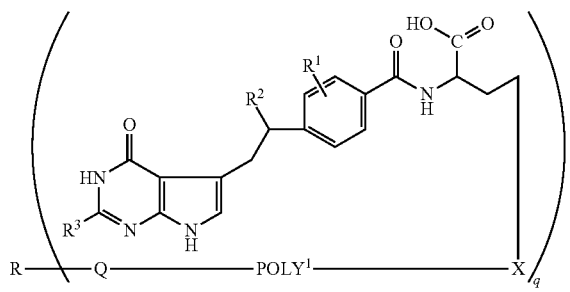

Formula I wherein:

R is a residue of polyol, polythiol or polyamine bearing from 3 to about 50 hydroxyl, thiol or amino groups;

$R^1$ is selected from the group consisting of H, halo (e.g., chloro and fluoro), methyl, methoxy and trifluoromethyl (and is preferably H);

$R^2$ is selected from the group consisting of H and methyl (and is preferably H);

$R^3$ is selected from the group consisting of H, lower alkyl and amino;

Q is a linker (and, in one or more embodiments, a hydrolytically stable linker);

$POLY^1$ is a water-soluble, non-peptidic polymer;

X is spacer moiety that includes a releasable linkage (e.g., a hydrolyzable linkage, an enzymatically degradable linkage, and so forth); and q is a positive integer from 3 to about 50 (e.g., 4), and pharmaceutically acceptable salts and solvates thereof.

Pharmaceutical Compositions of Conjugates of the Invention

The invention provides pharmaceutical compositions, both for veterinary and for human medical use, which comprise one or more multi-armed polymer conjugates of the invention or a pharmaceutically acceptable salt thereof, with one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants; preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80," and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy," $19^{th}$ ed., Williams & Williams, (1995), and in the "Physician's Desk Reference," $52^{nd}$ ed., Medical Economics, Montvale, N.J. (1998), and in "Handbook of Pharmaceutical Excipients," Third Ed., Ed. A. H. Kibbe, Pharmaceutical Press, 2000.

The conjugates may be formulated in compositions including those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. In general, the compositions are prepared by bringing the active compound into association with a liquid carrier to form a solution or a suspension, or alternatively, bringing the conjugate into association with formulation components suitable for forming a solid, optionally a particulate product, and then, if warranted, shaping the product into a desired delivery form. Solid formulations, when particulate, will typically comprise particles with sizes ranging from about 1 nanometer to about 500 microns. In general, for solid formulations intended for intravenous administration, particles will typically range from about 1 nm to about 10 microns in diameter. Particularly preferred are sterile, lyophilized compositions that are reconstituted in an aqueous vehicle prior to injection.

The amount of multi-armed polymer conjugate in the formulation will vary depending upon the specific active agent employed, its activity, the molecular weight of the conjugate, and other factors such as dosage form, target patient population, and other considerations, and will generally be readily determined by one skilled in the art. In practice, this will depending upon the particular conjugate, its activity, the severity of the condition to be treated, the patient, the stability of the formulation, and the like. Compositions will generally contain anywhere from about 1% by weight to about 99% by weight conjugate, typically from about 2% to about 95% by weight conjugate, and more typically from about 5% to 85% by weight conjugate, and will also depend upon the relative amounts of excipients/additives contained in the composition. More specifically, the composition will typically contain at least about one of the following percentages of conjugate: 2%, 5%, 10%, 20%, 30%, 40%, 50%, 60%, or more by weight.

Compositions of the present invention suitable for oral administration may be provided as discrete units such as capsules, cachets, tablets, lozenges, and the like, each containing a predetermined amount of the conjugate as a powder or granules; or a suspension in an aqueous liquor or non-aqueous liquid such as a syrup, an elixir, an emulsion, a draught, and the like.

Formulations suitable for parenteral administration conveniently comprise a sterile aqueous preparation of the prodrug conjugate, which can be formulated to be isotonic with the blood of the recipient.

Nasal spray formulations comprise purified aqueous solutions of the multi-armed polymer conjugate with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the multi-armed polymer conjugate dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol, e.g., by inhalation. These formulations comprise a solution or suspension of the desired multi-armed polymer conjugate or a salt thereof. The desired formulation may be placed in a small chamber and nebulized. Nebulization may be accomplished by compressed air or by ultrasonic energy to form a plurality of liquid droplets or solid particles comprising the conjugates or salts thereof.

Methods of Use

The multi-armed polymer conjugates provided herein can be used to treat or prevent any condition (e.g., cancer) responsive to administration of the conjugate described herein.

The multi-arm polymer conjugates of the invention are particularly useful as anticancer agents, i.e., an agent that can reduce the growth of one or more tumors. Exemplary cancer types include, but are not limited to, breast cancer, ovarian cancer, colon cancer, colorectal cancer, prostate cancer, gastric cancer, malignant melanoma, small cell lung cancer, non-small cell lung cancer, thyroid cancers, kidney cancer, cancer of the bile duct, brain cancer, cancer of the head and neck, lymphomas, leukemias, rhabdomyosarcoma, and neuroblastoma.

Methods of administration comprise administering to a mammal in need thereof a therapeutically effective amount of a composition or formulation containing a multi-arm polymer conjugate as provided herein. A therapeutically effective dosage amount of any specific multi-arm polymer conjugate will vary from conjugate to conjugate, patient to patient, and will depend upon factors such as the condition of the patient, the activity of the particular active agent employed, the route of delivery, and condition being treated.

Methods of treatment also include administering a therapeutically effective amount of a composition or formulation comprising a multi-arm polymer conjugate as described herein with a second anticancer agent (such as, for example, 5-fluorouracil, leucovorin, avastin, cetuximab, panitumumab, xeloda, abraxane, cis-platin, carboplatin and gemcitabine).

The multi-arm polymer conjugate of the invention may be administered once or several times a day, preferably once a day or less. Illustrative dosing schedules include once per week, once every two weeks, or once every three weeks. In the instance of a maintenance dose, dosing may take place even less frequently than once every three weeks, such as once monthly. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

The practice of the invention will employ, unless otherwise indicated, conventional techniques of organic synthesis and the like, which are within the skill of the art. Such techniques are fully described in the literature. Reagents and materials are commercially available unless specifically stated to the contrary. See, for example, M. B. Smith and J. March, *March's Advanced Organic Chemistry: Reactions Mechanisms and Structure*, 6th Ed. (New York: Wiley-Interscience, 2007), supra, and Comprehensive Organic Functional Group Transformations II, Volumes 1-7, Second Ed.: A Comprehensive Review of the Synthetic Literature 1995-2003 (Organic Chemistry Series), Eds. Katritsky, A. R., et al., Elsevier Science.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

The following examples illustrate certain aspects and advantages of the present invention, however, the present invention is in no way considered to be limited to the particular embodiments described below.

Example 1

Preparation of 4-Arm-PEG-γ-Amide-Pemetrexed Conjugates

4-Arm-PEG-γ-amide-pemetrexed conjugates were synthesized. The synthetic approach used can be divided in four parts, "Part A," "Part B," "Part C" and "Part D."

Part A—Preparation of the 4-Arm-PEG

The 4-arm-PEGs used in the synthesis of the 4-arm-PEG-γ-amide-pemetrexed conjugates were prepared in accordance with the general schematic provided below.

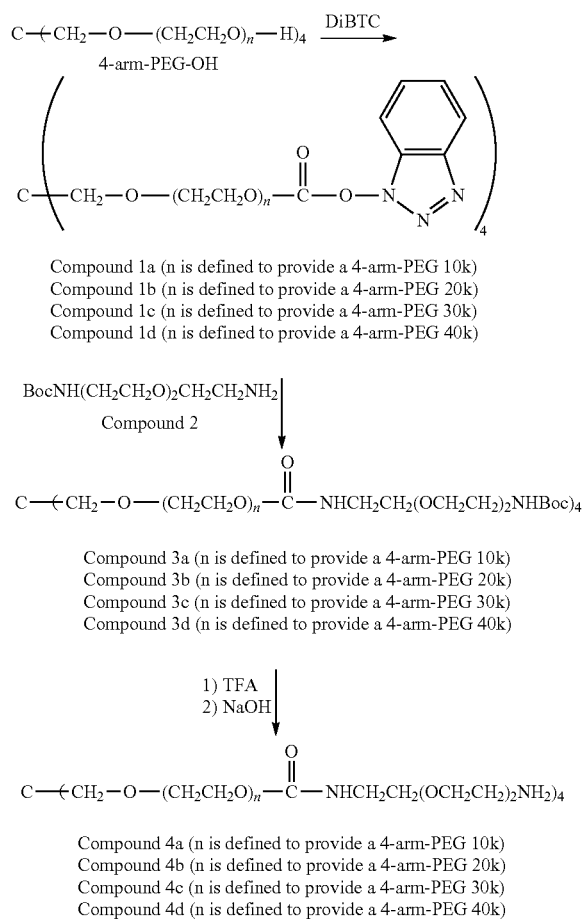

Compound 1a (n is defined to provide a 4-arm-PEG 10k)
Compound 1b (n is defined to provide a 4-arm-PEG 20k)
Compound 1c (n is defined to provide a 4-arm-PEG 30k)
Compound 1d (n is defined to provide a 4-arm-PEG 40k)

Compound 3a (n is defined to provide a 4-arm-PEG 10k)
Compound 3b (n is defined to provide a 4-arm-PEG 20k)
Compound 3c (n is defined to provide a 4-arm-PEG 30k)
Compound 3d (n is defined to provide a 4-arm-PEG 40k)

Compound 4a (n is defined to provide a 4-arm-PEG 10k)
Compound 4b (n is defined to provide a 4-arm-PEG 20k)
Compound 4c (n is defined to provide a 4-arm-PEG 30k)
Compound 4d (n is defined to provide a 4-arm-PEG 40k)

Synthesis of N-(t-Butoxycarbonyl)-2,2'-(Ethylenedioxy)bis(ethylamine), Compound 2

To a $CH_2Cl_2$ solution of 2,2-(ethylenedioxy)bis(ethylamine) (~120 g, 0.81 mol) at 0° C. in an ice bath was added a $CH_2Cl_2$ solution of di-t-butyl-dicarbonate (~60 g, 0.27 mol) with vigorous stirring. The reaction mixture was stirred at 0° C. for three hours. After solvent evaporation, the residue was dissolved in water and the solution was adjusted to pH=2 with $1.0NH_2SO_4$. The solution was washed twice with $CH_2Cl_2$, and then the pH was adjusted to 10 with solid NaOH and extracted with $CH_2Cl_2$. The combined $CH_2Cl_2$ phases were dried over $Na_2SO_4$. After evaporation, Compound 2 was obtained as a clear liquid (~35 g, 0.14 mol, ~52% yield). The product was confirmed by proton NMR.

Synthesis of 4-arm-$PEG_{10k}$-BTC, Compound 1a

To an acetonitrile solution of an azeotropically distilled 4-arm-$PEG_{10k}$-OH (~30 g, 3.0 mmol) was added pyridine (~3.9 mL, 48 mmol). After the solution was stirred at room temperature for 15 minutes, di-benzotriazole-carbonate (diBTC) (~11.8 g, 24 mmol) was added. The reaction mixture was then stirred at room temperature overnight (18 hours). Proton NMR showed that the reaction was complete. After solvent evaporation, the residue was dissolved in ~30 mL of $CH_2Cl_2$. The product $CH_2Cl_2$ solution was added to isopropanol (IPA) with vigorous stirring. The precipitate was collected by suction filtration, washed with IPA and dried in vacuo. 4-arm-$PEG_{10k}$-BTC, Compound 1a, was obtained as a white solid (~30.5 g, 2.9 mmol, ~97% yield).

Synthesis of 4-arm-$PEG_{20k}$-BTC, Compound 1b

To an acetonitrile solution of an azeotropically distilled 4-arm-$PEG_{20k}$-OH (~30 g, 1.5 mmol) was added pyridine (~2.0 mL, 24 mmol). After the solution was stirred at room temperature for 15 minutes, di-benzotriazole-carbonate (diBTC) (~6.0 g, 12 mmol) was added. The reaction mixture was then stirred at room temperature overnight (18 hours). Proton NMR showed that the reaction was complete. After solvent evaporation, the residue was dissolved in ~30 mL of $CH_2Cl_2$. The product $CH_2Cl_2$ solution was added to isopropanol (IPA) with vigorous stirring. The precipitate was collected by suction filtration, washed with IPA and dried in vacuo. 4-arm-$PEG_{20k}$-BTC, Compound 1b, was obtained as a white solid (~29.5 g, 1.4 mmol, ~96% yield).

Synthesis of 4-arm-$PEG_{30k}$-BTC, Compound 1c

To an acetonitrile solution of an azeotropically distilled 4-arm-$PEG_{30k}$-OH (~30 g, 1.0 mmol) was added pyridine (~1.6 mL, 20 mmol). After the solution was stirred at room temperature for 15 minutes, di-benzotriazole-carbonate (diBTC) (~5.4 g, 12 mmol) was added. The reaction mixture was then stirred at room temperature (17 hours). Proton NMR showed that the reaction was complete. After solvent evaporation, the residue was dissolved in ~30 mL of $CH_2Cl_2$. The product $CH_2Cl_2$ solution was added to isopropanol (IPA) with vigorous stirring. The precipitate was collected by suction filtration, washed with IPA and dried in vacuo. 4-arm-$PEG_{30k}$-BTC, Compound 1c, was obtained as a white solid (~26.8 g, 0.88 mmol, ~88% yield).

Synthesis of 4-arm-$PEG_{40k}$-BTC, Compound 1d

To an acetonitrile solution of an azeotropically distilled 4-arm-$PEG_{40k}$-OH (~30 g, 0.75 mmol) was added pyridine (~1.5 mL, 18 mmol). After the solution was stirred at room temperature 15 minutes, di-benzotriazole-carbonate (diBTC) (~5.4 g, 12 mmol) was added. The reaction mixture was then stirred at room temperature overnight (20 hours). Proton NMR showed that the reaction was complete. After solvent evaporation, the residue was dissolved in ~30 mL of $CH_2Cl_2$. The product $CH_2Cl_2$ solution was added to isopropanol (IPA) with vigorous stirring. The precipitate was collected by suction filtration, washed with IPA and dried in vacuo. 4-arm-$PEG_{40k}$-BTC, Compound 1d, was obtained as a white solid (~30.0 g, 0.74 mmol, ~93% yield).

Synthesis of 4-arm-$PEG_{10k}$-NHBoc, Compound 3a

To a $CH_2Cl_2$ solution of N-(t-butoxycarbonyl)-2,2'-(ethylenedioxy)bis(ethylamine) Compound 2 (~6.05 g, 24.4 mmol) was added triethylamine (TEA) (~6.8 mL, 48.9 mmol) and 4-arm-$PEG_{10k}$-BTC, Compound 1a (~30.5 g, 2.9 mmol). The solution was stirred at room temperature under $N_2$ for two hours and proton NMR indicated that the reaction was complete. The solvent was evaporated and the residue was precipitated in IPA to give 4-arm-$PEG_{10k}$-NHBoc, Compound 3a, as a white solid (~30.5 g, 2.8 mmol, ~96% yield).

Synthesis of 4-arm-$PEG_{20k}$-NHBoc, Compound 3b

To a $CH_2Cl_2$ solution of N-(t-butoxycarbonyl)-2,2'-(ethylenedioxy)bis(ethylamine) Compound 2 (~3.0 g, 12 mmol)

was added triethylamine (TEA) (~3.4 mL, 24 mmol) and 4-arm-PEG$_{20k}$-BTC, Compound 1b (~29.5 g, 1.48 mmol). The solution was stirred at room temperature under N$_2$ for two hours and proton NMR indicated that the reaction was complete. The solvent was evaporated and the residue was precipitated in IPA to give 4-arm-PEG$_{20k}$-NHBoc, Compound 3b, as a white solid (~30.6 g, 1.40 mmol, ~95% yield).

Synthesis of 4-arm-PEG$_{30k}$-NHBoc, Compound 3c

To a CH$_2$Cl$_2$ solution of N-(t-butoxycarbonyl)-2,2'-(ethylenedioxy)bis(ethylamine) Compound 2 (~1.75 g, 7.1 mmol) was added triethylamine (TEA) (~2.0 mL, 14.4 mmol) and 4-arm-PEG$_{30k}$-BTC, Compound 1c (~26.5 g, 0.87 mmol). The solution was stirred at room temperature under N$_2$ for two hours and proton NMR indicated that the reaction was complete. The solvent was evaporated and the residue was precipitated in IPA to give 4-arm-PEG$_{30k}$-NHBoc, Compound 3c, as a white solid (~26.0 g, 0.84 mmol, ~96% yield).

Synthesis of 4-arm-PEG$_{40k}$-NHBoc, Compound 3d

To a CH$_2$Cl$_2$ solution of N-(t-butoxycarbonyl)-2,2'-(ethylenedioxy)bis(ethylamine) Compound 2 (~1.9 g, 7.7 mmol) was added triethylamine (TEA) (~2.1 mL, 15.1 mmol) and 4-arm-PEG$_{40k}$-BTC, Compound 1d, (~30.0 g, 0.74 mmol). The solution was stirred at room temperature under N$_2$ for two hours and proton NMR indicated that the reaction was complete. The solvent was evaporated and the residue was precipitated in IPA to give 4-arm-PEG$_{40k}$-NHBoc, Compound 3d, as a white solid (~30.0 g, 0.73 mmol, ~99% yield).

Synthesis of 4-arm-PEG$_{10k}$-NH$_2$, Compound 4a

To a CH$_2$Cl$_2$ (~200 mL) solution of 4-arm-PEG$_{10k}$-NH-Boc, Compound 3a (~30.5 g, 2.8 mmol) was added 100 mL of trifluoroacetic acid (TFA). The reaction solution was stirred at room temperature under N$_2$ for two hours and proton NMR indicated that the reaction was complete. The solvent was evaporated and the residue was dried under vacuum overnight. The residue was dissolved in ~400 mL of water and ~50 g of NaCl was added. The aqueous solution was adjusted to pH=11 with 1.0 N NaOH and extracted with CH$_2$Cl$_2$ three times. The combined CH$_2$Cl$_2$ phases were dried over Na$_2$SO$_4$, evaporated and precipitated from Et$_2$O to give 4-arm-PEG$_{10k}$-NH$_2$, Compound 4a as a white solid (~28.1 g, 2.65 mmol, ~95% yield). Proton NMR confirmed product structure and showed that the amine substitution was ~92%.

Synthesis of 4-arm-PEG$_{20k}$-NH$_2$, Compound 4b

To a CH$_2$Cl$_2$ (~200 mL) solution of 4-arm-PEG$_{20k}$-NH-Boc, Compound 3 a (~29.5 g, 1.4 mmol) was added 100 mL of trifluoroacetic acid (TFA). The reaction solution was stirred at room temperature under N$_2$ for two hours and proton NMR indicated that the reaction was complete. The solvent was evaporated and the residue was dried under vacuum overnight. The residue was dissolved in ~400 mL of water and ~50 g of NaCl was added. The aqueous solution was adjusted to pH=11 with 1.0 N NaOH and extracted with CH$_2$Cl$_2$ three times. The combined CH$_2$Cl$_2$ phases were dried over Na$_2$SO$_4$, evaporated and precipitated from Et$_2$O to give 4-arm-PEG$_{20k}$-NH$_2$, Compound 4b as a white solid (~28.0 g, 1.36 mmol, ~97% yield). Proton NMR confirmed product structure and showed that the amine substitution was ~92%.

Synthesis of 4-arm-PEG$_{30k}$-NH$_2$, Compound 4c

To a CH$_2$Cl$_2$ (~150 mL) solution of 4-arm-PEG$_{30k}$-NH-Boc, Compound 3c (~26.0 g, 0.84 mmol) was added 150 mL of trifluoroacetic acid (TFA). The reaction solution was stirred at room temperature under N$_2$ for two hours and proton NMR indicated that the reaction was complete. The solvent was evaporated and the residue was dried under vacuum overnight. The residue was dissolved in ~300 mL of water and ~30 g of NaCl was added. The aqueous solution was adjusted to pH=11 with 2.0 N NaOH and extracted with CH$_2$Cl$_2$ three times. The combined CH$_2$Cl$_2$ phases were dried over Na$_2$SO$_4$, evaporated and precipitated from Et$_2$O to give 4-arm-PEG$_{30k}$-NH$_2$, Compound 4c, as a white solid (~23.6 g, 7.7 mmol, ~92% yield). Proton NMR confirmed product structure and showed that the amine substitution was ~92%.

Synthesis of 4-arm-PEG$_{40k}$-NH$_2$, Compound 4d

To a CH$_2$Cl$_2$ (~150 mL) solution of 4-arm-PEG$_{40k}$-NH-Boc, Compound 3d (~30.0 g, 0.73 mmol) was added 150 mL of trifluoroacetic acid (TFA). The reaction solution was stirred at room temperature under N$_2$ for two hours and proton NMR indicated that the reaction was complete. The solvent was evaporated and the residue was dried under vacuum overnight. The residue was dissolved in ~300 mL of water and ~30 g of NaCl was added. The aqueous solution was adjusted to pH=11 with 2.0 N NaOH and extracted with CH$_2$Cl$_2$ three times. The combined CH$_2$Cl$_2$ phases were dried over Na$_2$SO$_4$, evaporated and precipitated from Et$_2$O to give 4-arm-PEG$_{40k}$-NH$_2$, Compound 4d as a white solid (~28.0 g, 0.69 mmol, ~94% yield). Proton NMR confirmed product structure and showed that the amine substitution was ~94%.

Part B—Preparation of a Pemetrexed Precursor

A pemetrexed precursor used in the synthesis of the conjugates was prepared in accordance with the general schematic provided below.

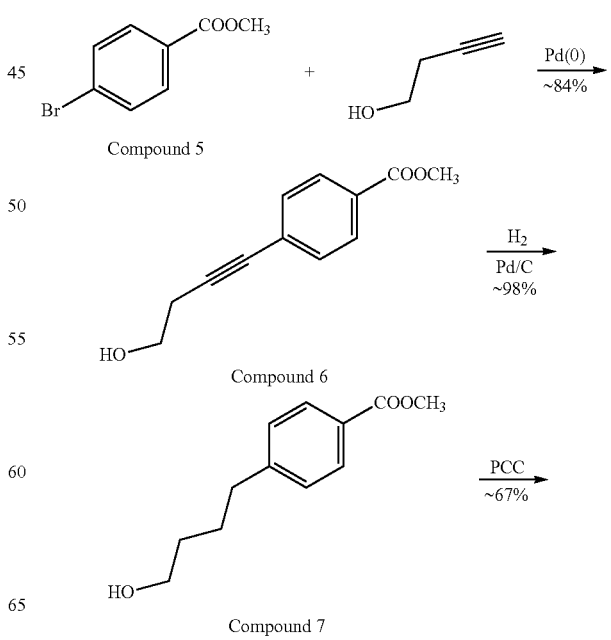

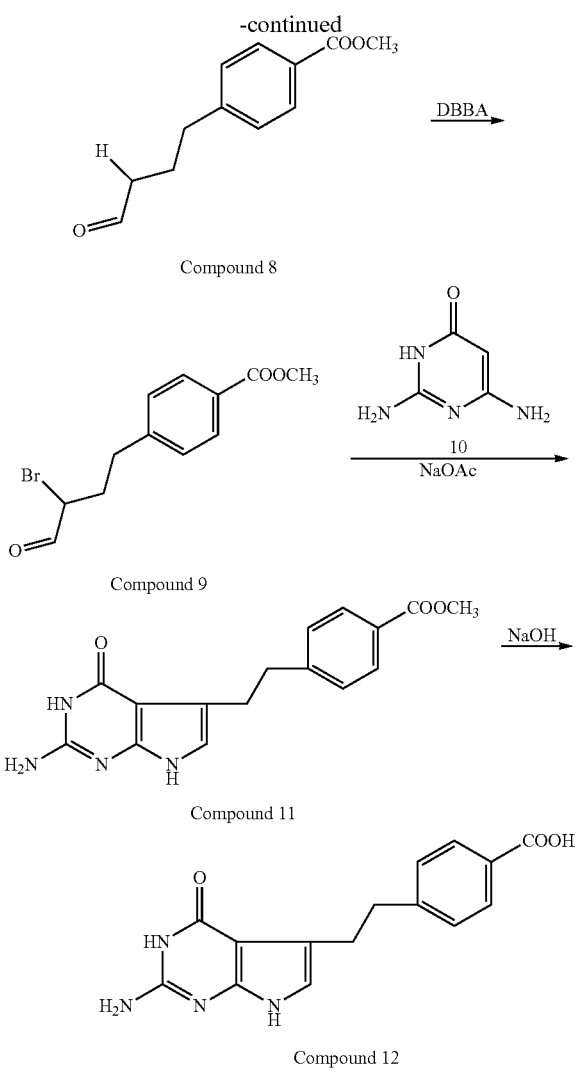

Compound 8

Compound 9

Compound 11

Compound 12

Synthesis of 4-(4-Hydroxy-1-Butynyl)benzoic Acid Methyl Ester, Compound 6

To an ethyl acetate (~50 mL) solution of methyl 4-bromobenzoate, Compound 5 (~5.0 g, 23.3 mmol) was added palladium chloride (~25 mg, 0.14 mmol), triphenylphosphine (~73 mg, 0.28 mmol), cuprous iodide (~53 mg, 0.28 mmol), diethylamine (~5.6 g, 76.9 mmol) and 3-butyn-1-ol (~2.1 g, 30.3 mmol). The reaction mixture was heated in an oil bath at 50° C. for four hours. After being cooled to room temperature, the solution was filtered; the filtrate was washed with 2N NaHSO$_4$ solution, then NaCl. Na$_2$SO$_4$ and silica gel were added into ethyl acetate solution, the slurry was stirred for 15 minutes and then filtered. The filtrate was concentrated to ~20 mL, then ~100 mL hexane was added and the reaction kept at 0-5° C. for about one hour. During cooling, a white solid precipitated from the solution which was collected by filtration, washed with cold hexane and dried in vacuo. $^1$H NMR showed that the light yellow solid was pure Compound 6 (~4.0 g, ~84% isolated yield).

Synthesis of 4-(4-Hydroxybutyl)benzoic Acid Methyl Ester, Compound 7

The CH$_2$Cl$_2$ solution of Compound 6 (~2.5 g, 12.2 mmol) was circulated through a 10% Pd/C cartridge of an H-Cube hydrogenation instrument (H$_2$ pressure: 50 bar; temperature: 30° C.; flow rate: 1.0 mL/min) until the reaction was complete as indicated by TLC. After solvent removal, a colorless liquid was obtained (~2.5 g, 12.0 mmol, ~98% isolated yield). Proton NMR indicated the desired product Compound 7 was prepared without any impurity.

Synthesis of 4-(4-butylaldehyde)benzoic Acid Methyl Ester, Compound 8

To a CH$_2$Cl$_2$ solution of Compound 7 (~1.5 g, 7.2 mmol) was added sodium acetate (~590 mg, 7.2 mmol) and pyridine chlorochromate (PCC) (~2.3 g, 10.8 mmol). The reaction mixture was stirred at room temperature for five hours. TLC showed that almost all starting material had been consumed. The product was then isolated as a clear liquid with Biotage flash chromatography using EtOAc/Hexane as eluents (~1.0 g, 4.8 mmol, ~67% isolated yield). Proton NMR confirmed that it was pure aldehyde product, Compound 8.

Synthesis of 4-(3-bromo-4-butylaldehyde)benzoic Acid Methyl Ester, Compound 9

To a CH$_2$Cl$_2$ solution of freshly prepared aldehyde product, Compound 8 (~1.0 g, 4.8 mmol) was added 5,5-dibromobarbituric acid (DBBA) (~828 mg, 2.9 mmol) and ~0.05 mL of 30% hydrobromic acid in acetic acid. The solution was stirred at room temperature overnight (16 hours). The reaction mixture was filtered. The CH$_2$Cl$_2$ filtrate was washed with 1N sodium thiosulfate, saturated sodium bicarbonate aqueous solution, NaCl solution and water, respectively. Proton NMR showed that the desired product, Compound 9, was obtained. Acetonitrile was added to product CH$_2$Cl$_2$ solution, and CH$_2$Cl$_2$ was then removed under reduced pressure. The resulting solution of Compound 9 in acetonitrile was taken to the next step reaction without further purification and isolation.

Synthesis of 4-[2-(2-Amino-4,7-dihydro-4-oxo-1H-pyrrolo[2,3-d]pyrimidin-5-yl)ethyl]benzoic Acid Methyl Ester, Compound 11

To the acetonitrile solution of Compound 9, prepared above, was added water, 2,4-diamino-6-hydroxypyrimidine (Compound 10) (~484 mg, 3.84 mmol) and sodium acetate (~630 mg, 7.7 mmol). The reaction mixture was heated in a water bath at 40° C. for three hours. The precipitate was collected by centrifugation, washed with 1:1 acetonitrile/water and dried in vacuo. Proton NMR confirmed that it was highly pure Compound 11.

Synthesis of 4-[2-(2-Amino-4,7-dihydro-4-oxo-1H-pyrrolo[2,3-d]pyrimidin-5-yl)ethyl]benzoic Acid, Compound 12

Compound 11 from the previous step was added to 1N NaOH solution (~15 mL). The reaction mixture was heated in a water bath at 40° C. for 1.5 hours. The suspension gradually became a clear orange solution. Then ethanol (~25 mL) was added to the reaction mixture, and the mixture cooled to room temperature. The pH of the solution was adjusted to 4.4 with 4N HCl with stirring and a white solid quickly precipitated from the solution. The precipitate was collected by centrifugation, washed with 1:1 ethanol/water and dried in vacuo. Compound 12 was obtained as a light purple solid (~670 mg, 2.2 mmol, ~47% three step overall isolated yield based on Compound 8). Proton NMR confirmed the product structure.

Part C—Preparation of a Glutamyl Reagent

A glutamyl reagent used in the synthesis of the conjugates was prepared in accordance with the general schematic provided below.

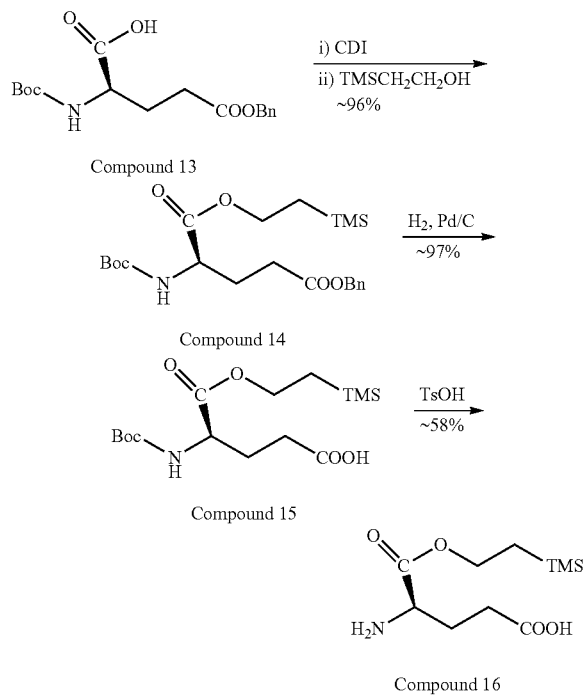

Compound 13

Compound 14

Compound 15

Compound 16

Synthesis of N-(t-Butoxycarbonyl)-α-[2-(trimethylsilyl)ethyoxy]-γ-benzyl-L-glutamate 14

After a $CH_2Cl_2$ solution of N-(t-butoxycarbonyl)-γ-benzyl-L-glutamic acid, Compound 13 (~5.0 g, 14.8 mmol) and carbonyldiimidazole (CDI) (~2.64 g, 16.3 mmol) was stirred at room temperature one hour, 2-(trimethylsilyl)ethanol (~1.93 g, 16.3 mmol) was added, and the reaction mixture was further stirred at room temperature overnight (20 hours). The reaction solution was then washed with an aqueous NaCl solution, dried over $Na_2SO_4$, and the solvent removed under reduced pressure. Purification by Biotage flash chromatography (EtOAc/Hexane) gave the desired Compound 14 as a colorless liquid (~6.2 g, 14.2 mmol, ~96% isolated yield). Proton NMR confirmed the product structure.

Synthesis of N-(t-Butoxycarbonyl)-α-[2-(trimethylsily)ethyoxy]-L-glutamic Acid, Compound 15

Into an ethanol solution of Compound 14 (~6.2 g, 14.2 mmol) and 10% Pd/C (~0.5 g) was bubbled hydrogen gas produced by the H-Cube at room temperature overnight (20 hours). TLC showed that the reaction was complete. Purification by Biotage flash chromatography ($CH_2Cl_2/CH_3OH$) gave the desired product a clear liquid was obtained (~4.8 g, 13.8 mmol, ~97% isolated yield). Proton NMR indicated that it was pure Compound 15.

Synthesis of α-[2-(Trimethylsily)ethyoxy]-L-glutamic Acid, Compound 16

To a water/dioxane (1:3) solution of Compound 15 (~3.0 g, 8.65 mmol) was added p-$TsOH.H_2O$ (~2.47 g, 13.0 mmol) and the solution was heated in an oil bath for three hours. After being cooled to room temperature, Dowex 1×8 ($HCO_3^-$ form, ~12 g) was added and the suspension was stirred at room temperature for an additional thirty minutes. The resin was removed by filtration and the remaining filtrate was evaporated to give a white solid. Purification by Biotage flash chromatography ($CH_2Cl_2/CH_3OH$) gave the desired product, Compound 16 as a white solid (~1.23 g, 4.98 mmol, ~58% isolated yield). Proton NMR confirmed the product structure.

Part D—Final Preparation of Conjugates

Final preparation of the conjugates followed the general schematic provided below (wherein the final preparation uses compounds prepared from Part A, Part B and Part C).

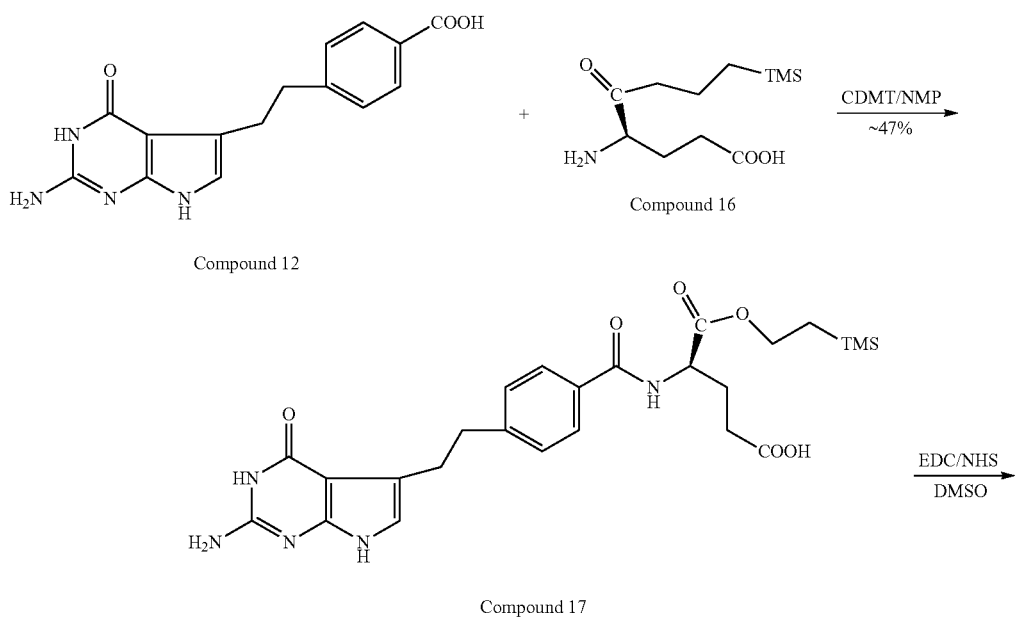

Compound 12

Compound 16

Compound 17

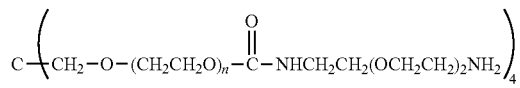

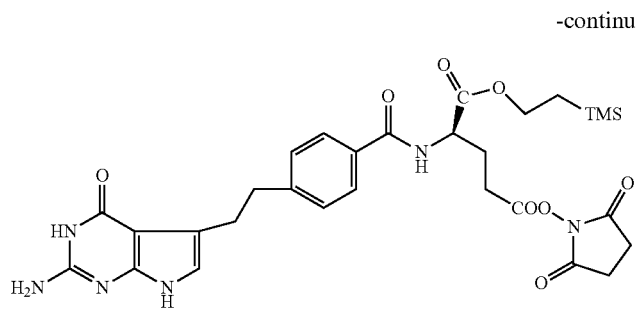

Compound 18

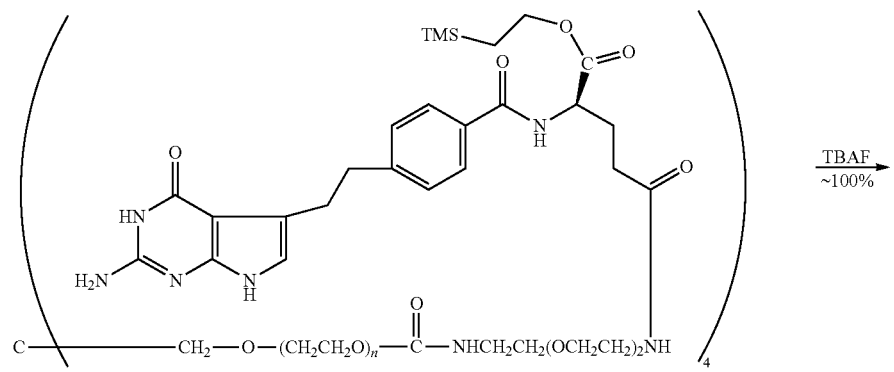

Compound 19a (n is defined to provide a 4-arm-PEG 10 k)
Compound 19b (n is defined to provide a 4-arm-PEG 20 k)
Compound 19c (n is defined to provide a 4-arm-PEG 30 k)
Compound 19d (n is defined to provide a 4-arm-PEG 40 k)

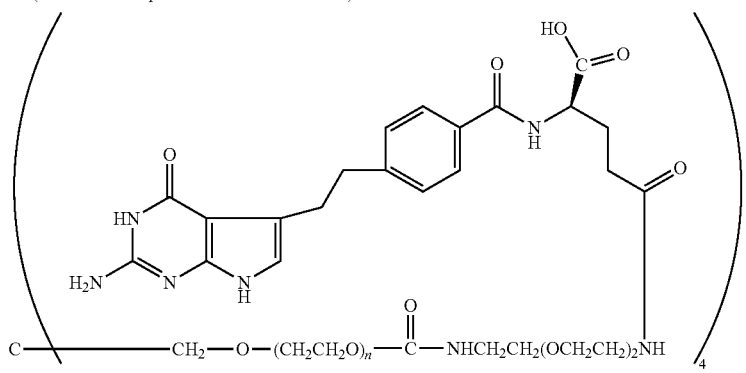

Compound 20a (n is defined to provide a 4-arm-PEG 10 k)
Compound 20b (n is defined to provide a 4-arm-PEG 20 k)
Compound 20c (n is defined to provide a 4-arm-PEG 30 k)
Compound 20d (n is defined to provide a 4-arm-PEG 40 k)

Synthesis of N-[4-[2-(2-Amino-4,7-dihydro-4-oxo-1H-pyrrolo[2,3-d]-pyrimidin-5-yl)ethyl]benzoyl]-α-[2-(trimethylsilyl)ethyoxy]-L-glutamic Acid, Compound 17

To a suspension of Compound 12 (~880 mg, 2.94 mmol) in DMF was added N-methylmorpholine (~892 mg, 8.82 mmol) and 2-chloro-4,6-dimethoxy-1,3,5-triazine (CDMT) (~516 mg, 2.94 mmol). The reaction mixture was stirred at room temperature for one hour and then N-[2-(trimethylsilyl)ethyoxy]-L-glutamic acid Compound 16 (~726 mg, 2.94 mmol) was added. The reaction mixture was stirred at room temperature for an additional three hours until analysis by HPLC indicated that the reaction was complete. Then $CH_2Cl_2$ (~300 mL) and 1M acetic acid (~300 mL) was added to the reaction mixture, and the resulting mixture was stirred for 15 minutes. The $CH_2Cl_2$ phase was washed with $H_2O/CH_3OH$/1M HOAc (2:1:1) and $H_2O/CH_3OH$ (2:1), dried over $Na_2SO_4$ and the solvent removed under reduced pressure to give crude product. Purification by Biotage flash chromatography ($CH_2Cl_2$, 0.1% HOAc/$CH_3OH$) gave the desired product, Compound 17 (~1.0 g, 1.89 mmol, ~64% isolated yield). Proton NMR confirmed the product structure.

Synthesis of 4-arm-PEG$_{10k}$-γ-amide-Pemetrexed Conjugate, Compound 20a

To a DMSO solution of α[2-(trimethylsilyl)ethyoxy]-pemetrexed Compound 17 (~276 mg, 0.52 mmol) was added N-hydroxysuccinimide (~90 mg, 0.78 mmol) and N-ethyl-N'-(3-dimethylaminopropyl)carbodiimide (EDC.HCl) (~498 mg, 2.6 mmol). The reaction mixture was stirred at room temperature overnight (17 hours) until HPLC showed that the reaction was complete to give Compound 18. Then, Compound 4a (~1.01 g, 0.087 mmol) and triethylamine (TEA) (~525 mg, 5.2 mmol) were added to the reaction mixture and the resulting mixture was stirred at room temperature for an additional three hours until HPLC analysis showed that the desired PEG-pemetrexed conjugate was formed as indicated by both UV (pemetrexed) and ELSD (PEG) absorptions. The reaction solution was poured into a 1:2 mixture of IPA/Et$_2$O with vigorous stirring with the PEG-pemetrexed conjugate Compound 19a precipitating. The precipitate was collected by suction filtration and dried in vacuo. The crude product Compound 19a was dissolved in DMSO and ~5.2 mL of tetrabutylammonium fluoride solution (TBAF) in THF was added. The mixture was stirred at room temperature overnight (17 hours). Proton NMR showed that the reaction was complete. The final conjugate 4-arm-PEG$_{10k}$-γ-amide-pemetrexed Compound 20a was precipitated twice from 1:2 mixture of IPA/Et$_2$O, collected by suction filtration and dried in vacuo (~0.82 g, 0.064 mmol, ~73% yield). HPLC showed that the conjugate purity was >98% and no free pemetrexed was detected. Proton NMR confirmed the conjugate structure. The pemetrexed substitution was ~75% or pemetrexed loading was ~9.5 w/w % estimated from integration.

Synthesis of 4-arm-PEG$_{20k}$-γ-amide-Pemetrexed Conjugate, Compound 20b

To a DMSO solution of a[2-(trimethylsilyl)ethyoxy]-pemetrexed Compound 17 (~270 mg, 0.51 mmol) was added N-hydroxysuccinimide (~88 mg, 0.77 mmol) and N-ethyl-M-(3-dimethylaminopropyl)carbodiimide (EDC.HCl) (~320 mg, 1.7 mmol). The reaction mixture was stirred at room temperature for 4.5 hours until HPLC showed that the reaction was complete to give Compound 18. Then Compound 4b (~1.94 g, 0.085 mmol), EDC.HCl (~293 mg, 1.5 mmol) and triethylamine (TEA) (~309 mg, 3.1 mmol) were added to the reaction mixture and the resulting mixture was stirred at room temperature overnight (17 hours). HPLC analysis showed that PEG-pemetrexed conjugate was formed as indicated by both UV (pemetrexed) and ELSD (PEG) absorptions. The reaction solution was poured into a 1:1 mixture of IPA/Et$_2$O with vigorous stirring with the PEG-pemetrexed conjugate Compound 19b precipitating. The precipitate was collected by suction filtration and dried in vacuo. The crude product Compound 19b was then dissolved in DMSO and ~3.0 mL of tetrabutylammonium fluoride solution (TBAF) in THF was added. The mixture was stirred at room temperature overnight (18 hours). Proton NMR showed that all the 2-(trimethylsilyl)ethyoxyl groups were removed. The final conjugate of 4-arm-PEG$_{20k}$-γ-amide-pemetrexed, Compound 20b was precipitated twice from 1:1 mixture of IPA/Et$_2$O, collected by suction filtration and dried in vacuo (~1.7 g, 0.072 mmol, ~85% yield). HPLC showed that the conjugate purity was >98% and no free pemetrexed was detected. Proton NMR confirmed the conjugate structure. The pemetrexed substitution was ~55% or pemetrexed loading was ~4.0 w/w % estimated from integration.

Synthesis of 4-arm-PEG$_{30k}$-γ-amide-Pemetrexed Conjugate, Compound 20c

To a DMSO solution of α-[2-(trimethylsilyl)ethyoxy]-pemetrexed Compound 17 (~280 mg, 0.53 mmol) was added N-hydroxysuccinimide (~92 mg, 0.80 mmol) and N-ethyl-N-(3-dimethylaminopropyl)carbodiimide (EDC.HCl) (~500 mg, 2.6 mmol). The reaction mixture was stirred at room temperature overnight (17 hours) until HPLC showed that the reaction was complete to give compound Compound 18. Then, Compound 4c (~2.79 g, 0.089 mmol) and triethylamine (TEA) (~525 mg, 5.2 mmol) were added to the reaction mixture and the resulting mixture was stirred at room temperature for an additional 16 hours. HPLC analysis showed that the PEG-pemetrexed conjugate was formed as indicated by both UV (pemetrexed) and ELSD (PEG) absorptions. The reaction solution was poured into a 1:1 mixture of IPA/Et$_2$O with vigorous stirring with the PEG-pemetrexed conjugate Compound 19c precipitating. The precipitate was collected by suction filtration and dried in vacuo. The crude product Compound 19c was dissolved in DMSO and ~5.0 mL of tetrabutylammonium fluoride solution (TBAF) in THF was added. The mixture was stirred at room temperature overnight (18 hours). Proton NMR showed that the deprotection was complete. The final conjugate of 4-arm-PEG$_{30k}$-γ-amide-pemetrexed Compound 20c was precipitated twice from 1:1 mixture of IPA/Et$_2$O, collected by filtration and dried in vacuo (~2.5 g, 0.076 mmol, ~86% yield). HPLC showed that the conjugate purity was >98% and no free pemetrexed was detected. Proton NMR confirmed the conjugate structure. The pemetrexed substitution was ~70% or pemetrexed loading was ~3.7 w/w % estimated from integration.

Synthesis of 4-arm-PEG$_{40k}$-γ-amide-Pemetrexed Conjugate, Compound 20d

To a DMSO solution of α-[2-(trimethylsilyl)ethyoxy]-pemetrexed Compound 17 (~280 mg, 0.53 mmol) was added N-hydroxysuccinimide (~92 mg, 0.80 mmol) and N-ethyl-N'-(3-dimethylaminopropyl)carbodiimide (EDC.HCl) (~500 mg, 2.6 mmol). The reaction mixture was stirred at room temperature overnight (17 hours) until HPLC analysis showed that the reaction was complete to give Compound 18. Then Compound 4d (~3.86 g, 0.088 mmol) and triethylamine (TEA) (~530 mg, 5.3 mmol) were added to the reaction mixture and the resulting mixture was stirred at room temperature for an additional 20 hours. HPLC analysis showed that PEG-pemetrexed conjugate was formed as indicated by both UV (pemetrexed) and ELSD (PEG) absorptions. The reaction solution was poured into a 1:1 mixture of IPA/Et$_2$O with strong stirring with the PEG-pemetrexed conjugate Compound 19d precipitating. The precipitate was collected by suction filtration and dried in vacuo. The crude product Compound 19d was dissolved in DMSO and ~5.0 mL of tetrabutylammonium fluoride solution (TBAF) in THF was added. The mixture was stirred at room temperature overnight (21 hours). Proton NMR showed that the deprotection was complete. The final conjugate of 4-arm-PEG$_{40k}$-γ-amide-pemetrexed Compound 20d was precipitated twice from 1:1 mixture of IPA/Et$_2$O, collected by filtration and dried in vacuo (~3.6 g, 0.080 mmol, ~91% yield). HPLC showed that the conjugate purity was >98% and no free pemetrexed was detected. Proton NMR confirmed the conjugate structure. The pemetrexed substitution was ~75% or pemetrexed loading was ~2.7 w/w % estimated from integration.

Example 2

Preparation of 4-Arm-PEG-γ-Ester-Pemetrexed Conjugates

4-Arm-PEG-γ-ester-pemetrexed conjugates (including 4-arm-PEG-γ-ethyl-ester-pemetrexed conjugates and 4-arm-PEG-γ-isopropyl-ester-pemetrexed conjugates) were synthesized.

With respect to the preparation of 4-arm-PEG-γ-ethyl-ester-pemetrexed conjugates, Compound 17 was prepared in accordance with "Part B," Part C" and the first reaction of "Part D" as described in Example 1. Thereafter, the synthetic approach described below was followed.

removed all DCM solvent, the product residue was dissolved in ethanol and added ~5 mL of 1N NaOH, the solution was stirred at room temperature for 18 hours. Thereafter, all solvents were removed and the residue was extracted with DCM three times. The extracted residue was then combined with the DCM phase and washed with NaCl solution once. Once the DCM phase was dried with $Na_2SO_4$ and all solvents were removed, a colorless liquid was obtained (~1.6 g, 7.80 mmol, ~41% isolated yield). $^1$H NMR ($CDCl_3$) indicated that it was pure Boc-2(2-aminoethoxy)ethanol.

Synthesis γ-Boc-2-(2-aminoethoxy)ethanol-ester-α-TMSE-pemetrexed (Compound 21). Compound 17 (~500 mg, ~0.95 mmol), Boc-2-(2-aminoethoxy)ethanol (~292 mg, ~1.41 mmol) and DMAP (~139 mg, ~1.14 mmol) were dissolved in DMF, then DCC (~782 mg, ~3.79 mmol) was added. The reaction mixture was stirred at room temperature for 20 hours and HPLC analysis indicated that almost all of

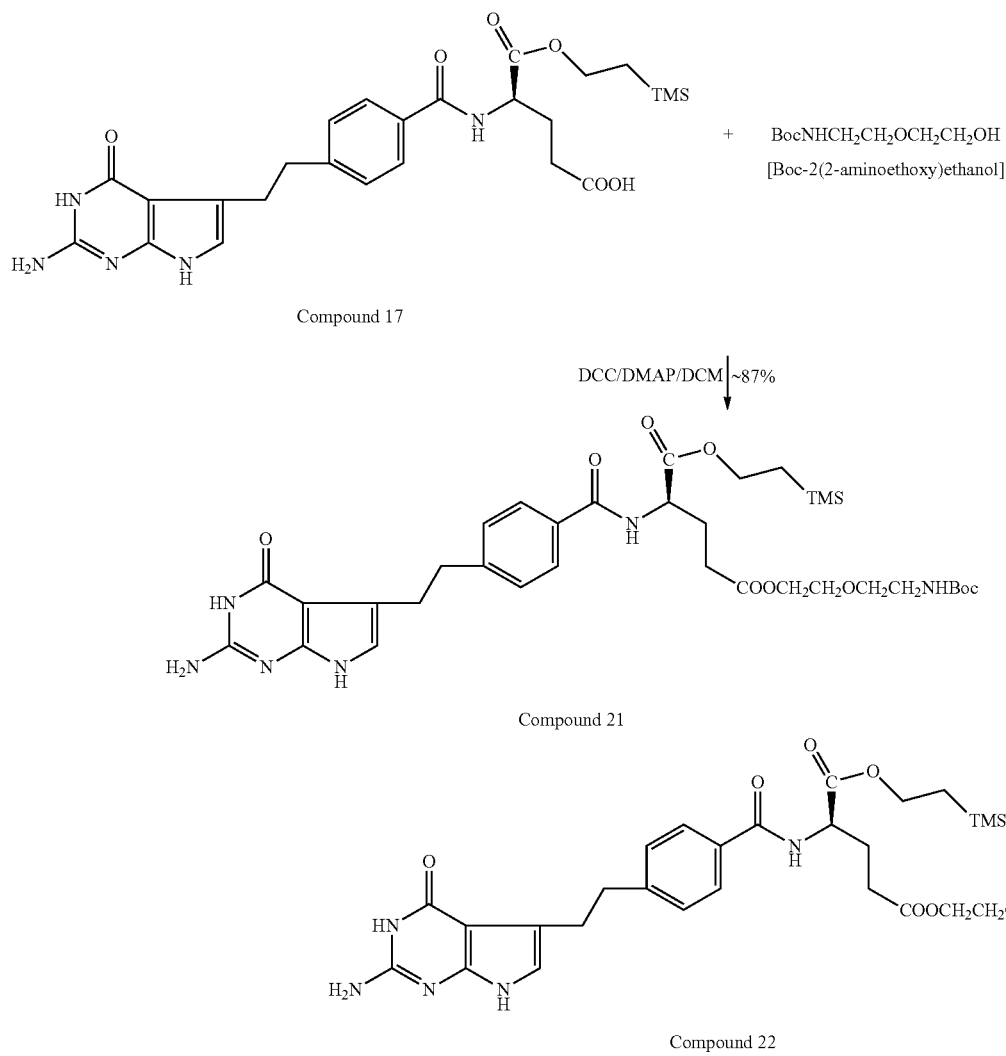

Compound 17

Compound 21

Compound 22

Synthesis of Boc-2(2-aminoethoxy)ethanol. To a DCM solution of 2-(2-aminoethoxy)ethanol (~2.0 g, ~19.02 mmol) was added di-tert-butyl-dicarbonate (~6.23 g, ~28.5 mmol) and TEA (~3.85 g, ~38.0 mmol), the reaction mixture was stirred at room temperature for three hours. After the starting material was reacted. Following filtration to remove DCU and then purification by Biotage (DCM/methanol), a light yellow liquid was obtained (~560 mg, ~0.783 mmol, ~83% isolated yield). Both HPLC and NMR confirmed the presence of Compound 21.

Synthesis γ-2-(2-aminoethoxy)ethanol-ester-α-TMSE-pemetrexed (Compound 22). To a DCM solution of γ-Boc-2-(2-aminoethoxy)ethanol-ester-α-TMSE-pemetrexed (Compound 21) (~360 mg, ~0.50 mmol), ~1.5 mL of TFA was added. The reaction mixture was stirred at room temperature for five hours. HPLC analysis indicated that the reaction was complete. The product was purified by Biotage using DCM and methanol as eluents, after work up, a white solid was obtained (~285 mg, ~0.46 mmol, ~92% isolated yield), and both HPLC and NMR confirmed that it was pure γ-2-(2-aminoethoxy)ethanol-ester-α-TMSE-pemetrexed (Compound 22).

Synthesis of 4-arm-PEG-20k-γ-Ethyl-Ester-α-TMSE-pemetrexed (Compound 23b). Azetropically distilled 4-Arm-PEG-20k-CM (~1.02 g, 0.051 mmol) was dissolved in DCM, γ-2-(2-aminoethoxy)ethanol-ester-α-TMSE-pemetrexed (Compound 22, ~150 mg, ~0.24 mmol), TEA (~123 mg, ~1.22 mmol), HOBt (~35 mg, ~0.26 mmol) and EDC (~190 mg, ~1.22 mmol) were added into the reaction solution. The reaction mixture was stirred at room temperature for 18 hours, and HPLC analysis indicated that the reaction was complete. The product was precipitated twice in a 1:1 IPA/Et$_2$O mixture and isolated by centrifugation. After dry-

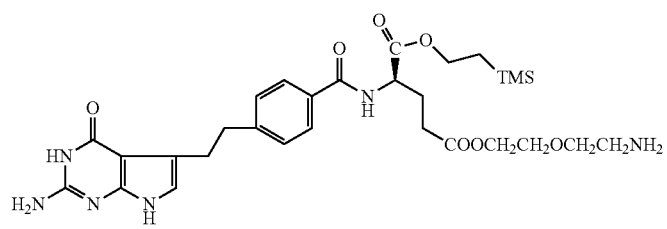

Compound 22

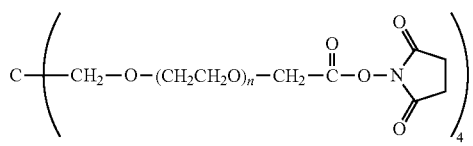

4-Arm-PEG 10k-CM (n is defined to provide a 4-arm-PEG 10k)
4-Arm-PEG 20k-CM (n is defined to provide a 4-arm-PEG 20k)
4-Arm-PEG 30k-CM (n is defined to provide a 4-arm-PEG 40k)

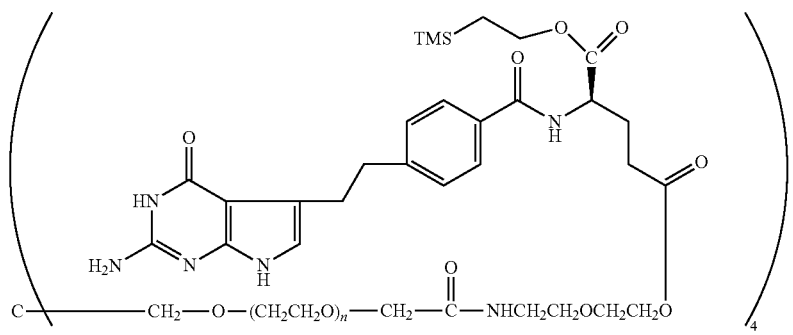

Compound 23a (n is defined to provide a 4-arm-PEG 10k)
Compound 23b (n is defined to provide a 4-arm-PEG 20k)
Compound 23c (n is defined to provide a 4-arm-PEG 40k)

Synthesis of 4-arm-PEG-10k-γ-Ethyl-Ester-α-TMSE-pemetrexed (Compound 23a). Azetropically distilled 4-Arm-PEG-10k-CM (~512 mg, 0.051 mmol) was dissolved in DCM, γ-2-(2-aminoethoxy)ethanol-ester-α-TMSE-pemetrexed (Compound 22, ~150 mg, ~0.24 mmol), TEA (~74 mg, ~0.73 mmol), HOBt (~35 mg, ~0.26 mmol) and EDC (114 mg, ~1.73 mmol) were added into the reaction solution. The reaction mixture was stirred at room temperature for 18 hours, and HPLC analysis indicated that the reaction was complete. The product was precipitated twice in a 1:1 IPA/Et$_2$O mixture and isolated by centrifugation. After drying via vacuum overnight, a white solid was obtained (~480 mg, ~94% recovery). HPLC indicated that it was pure Compound 23a conjugate without any small molecule impurities.

ing via vacuum overnight, Compound 23b was obtained as a white solid (~1.02 g, ~100% recovery).

Synthesis of 4-arm-PEG-40k-γ-Ethyl-Ester-α-TMSE-pemetrexed (Compound 23c). Azetropically distilled 4-Arm-PEG-40k-CM (~2.05 g, 0.051 mmol) was dissolved in DCM, γ-2-(2-aminoethoxy)ethanol-ester-α-TMSE-pemetrexed (Compound 22, ~150 mg, ~0.24 mmol), TEA (~123 mg, ~1.22 mmol), HOBt (~35 mg, ~0.26 mmol) and EDC (~190 mg, ~1.22 mmol) were added into the reaction solution. The reaction mixture was stirred at room temperature for 22 hours, and HPLC analysis indicated that the reaction was complete. The product was precipitated twice in a 1:1 IPA/Et$_2$O mixture and isolated by centrifugation. After drying via vacuum overnight, Compound 23c was obtained as a white solid (~2.05 g, ~100% recovery).

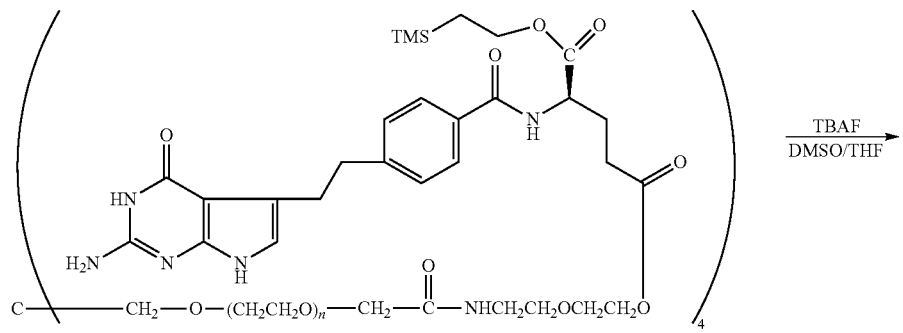

Compound 23a (n is defined to provide a 4-arm-PEG 10k)
Compound 23b (n is defined to provide a 4-arm-PEG 20k)
Compound 23c (n is defined to provide a 4-arm-PEG 40k)

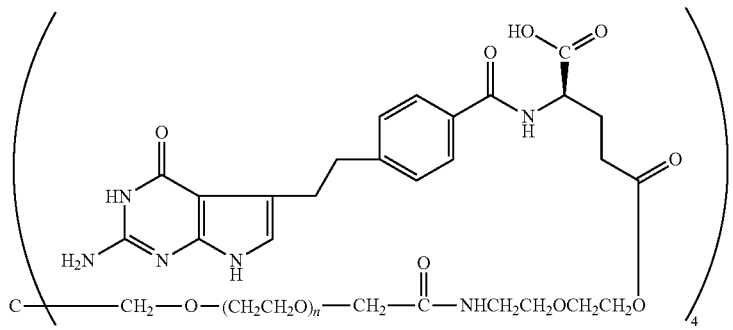

Compound 24a (n is defined to provide a 4-arm-PEG 10k)
Compound 24b (n is defined to provide a 4-arm-PEG 20k)
Compound 24c (n is defined to provide a 4-arm-PEG 40k)

Synthesis of 4-arm-PEG-10k-γ-Ethyl-Ester-pemetrexed (Compound 24a). To a DMF solution of 4-arm-PEG-10 k-γ-ethyl-ester-α-TMSE-pemetrexed (Compound 23a, ~500 mg) was added ~1.5 mL of 1.0M TBAF THF solution. The reaction mixture was stirred at room temperature for seven hours. HPLC analysis indicated that the reaction was complete. The product was precipitated from a 1:1 IPA/Et$_2$O mixture three times and isolated by centrifugation. A white solid was obtained (~500 mg). HPLC and NMR confirmed that it was 4-arm-PEG-10k-γ-ethyl-ester-pemetrexed (Compound 24a), the drug substitution was ~87%.

Synthesis of 4-arm-PEG-20k-γ-Ethyl-Ester-pemetrexed (Compound 24b). To a DMF solution of 4-arm-PEG-20k-γ-ethyl-ester-α-TMSE-pemetrexed (Compound 23b, ~1.02 g) was added ~1.5 mL of 1.0M TBAF THF solution. The reaction mixture was stirred at room temperature for 24 hours. HPLC analysis indicated that the reaction was complete. The product was first dissolved DCM and washed with a 0.1N HCl/NaCl water solution to remove excess TBAF, however, an emulsion was formed, which induced some product loss. The product was then precipitated from a 1:1 IPA/Et$_2$O mixture three times and isolated by centrifugation. A white solid was obtained (~491 mg, ~49% isolated yield). HPLC and NMR confirmed that it was 4-arm-PEG-20k-γ-ethyl-ester-pemetrexed (Compound 24b), the drug substitution was ~57%.

Synthesis of 4-arm-PEG-40k-γ-Ethyl-Ester-pemetrexed (Compound 24c). To a DMF solution of 4-arm-PEG-40k-γ-ethyl-ester-α-TMSE-pemetrexed (Compound 23c, ~2.05 g) was added ~2.0 mL of 1.0M TBAF THF solution. The reaction mixture was stirred at room temperature for 23 hours. HPLC analysis indicated that the reaction was complete. The product was first dissolved DCM and washed twice with a 0.1N HCl/NaCl water solution to remove excess TBAF, however, an emulsion was formed, which induced some product loss. The product was then precipitated from a 1:1 IPA/Et$_2$O mixture three times and isolated by centrifugation. A white solid was obtained (~1.2 g, ~60% isolated yield). HPLC and NMR confirmed that it was 4-arm-PEG-40k-γ-ethyl-ester-pemetrexed (Compound 24c), the drug substitution was ~36%.

With respect to the preparation of 4-arm-PEG-γ-isopropyl-ester-pemetrexed conjugates, Compound 17 was prepared in accordance with "Part B," Part C" and the first reaction of "Part D" as described in Example 1. Thereafter, the synthetic approach and hydrolysis described below was followed.

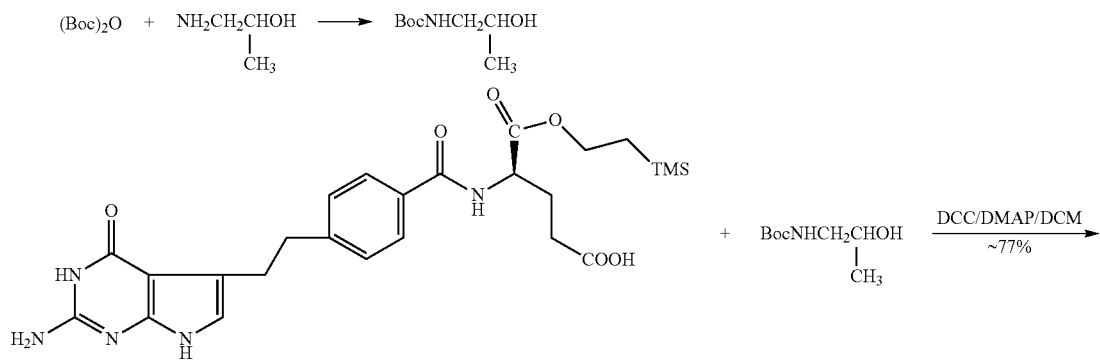
Compound 17
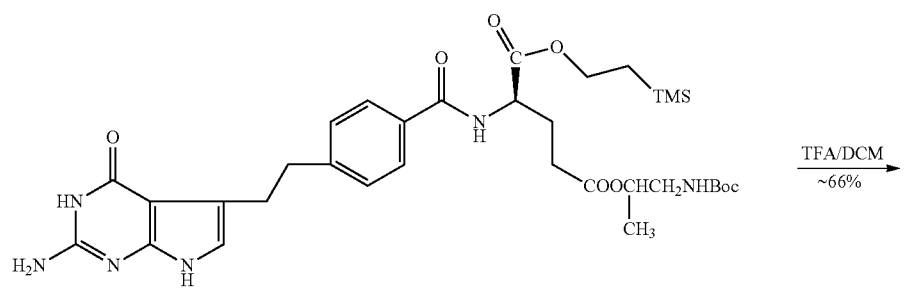
Compound 25
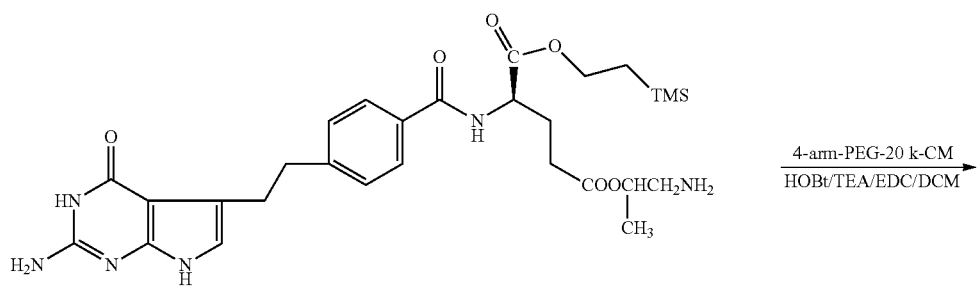
Compound 26
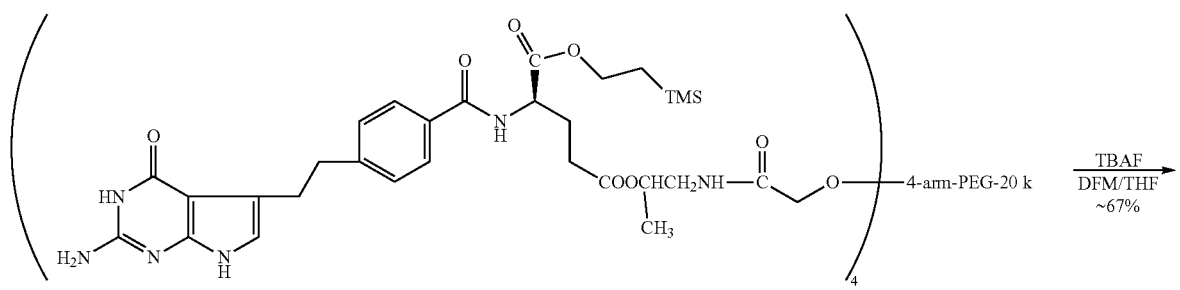
Compound 27
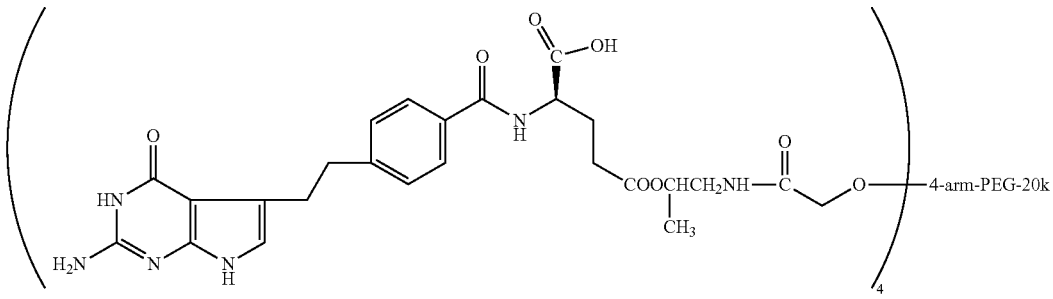
Compound 28

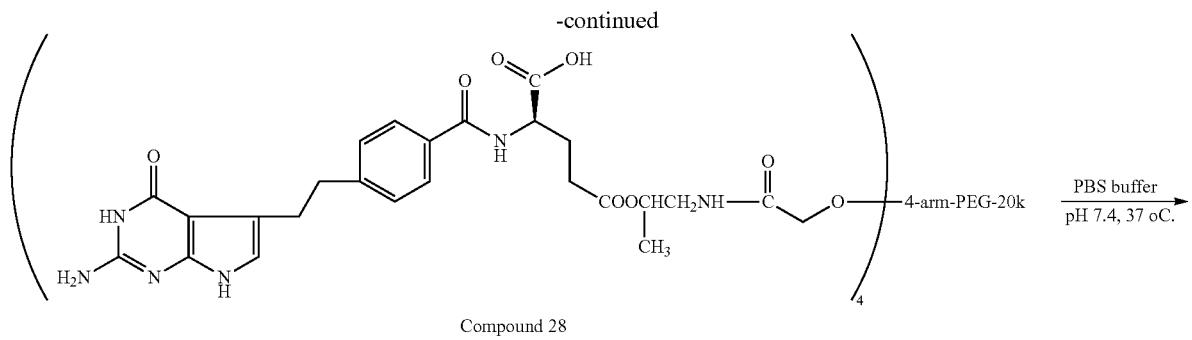

Compound 28

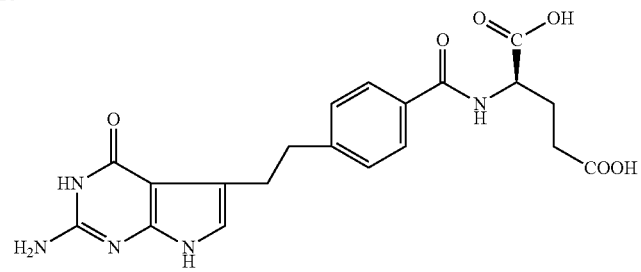

Synthesis of Boc-amino-2-propanol. To a DCM solution of amino-2-propanol (~5.0 g, ~66.6 mmol) was slowly added di-tert-butyl-dicarbonate (~14.6 g, ~66.6 mmol). The reaction mixture was stirred at room temperature for 18 hours. The DCM solution was washed with NaCl solution three times. The DCM phase was dried with $Na_2SO_4$ and all solvents were removed. Boc-amino-2-propanol was obtained as a colorless liquid (~11.1 g, 63.3 mmol, ~95% isolated yield).

Synthesis γ-Boc-amino-2-propanol-ester-α-TMSE-pemetrexed (Compound 25). α-TMSE-pemetrexed (Compound 17, ~250 mg, ~0.47 mmol), Boc-amino-2-propanol (~125 mg, ~0.71 mmol) and DMAP (~70 mg, ~0.57 mmol) were dissolved in DMF, and then DCC (~489 mg, ~2.37 mmol) was added. The reaction mixture was stirred at room temperature for 24 hours and HPLC analysis indicated that almost all starting material was consumed. After filtration to remove DCU and purification by Biotage (DCM/methanol), a white solid was obtained (~250 mg, ~0.37 mmol, ~77% isolated yield). LC-MS (Calc: 684; Found: 684) confirmed it was γ-Boc-amino-2-propanol-ester-α-TMSE-pemetrexed (Compound 25).

Synthesis γ-amino-2-propanol-ester-α-TMSE-pemetrexed (Compound 26). To a DCM solution of γ-Boc-amino-2-propanol-ester-α-TMSE-pemetrexed (Compound 25, ~250 mg, ~0.37 mmol), TFA (~1.0 mL) was added. The reaction mixture was stirred at room temperature for 20 hours and HPLC analysis indicated that the reaction was complete. The product was purified by Biotage using DCM and methanol as eluents; after work up, a white solid was obtained (~140 mg, ~0.24 mmol, ~66% isolated yield), HPLC confirmed that it was pure γ-amino-2-propanol-ester-α-TMSE-pemetrexed (Compound 23).

Synthesis of 4-arm-PEG-20k-γ-isopropanyl-ester-α-TMSE-pemetrexed (Compound 27). Azetropically distilled 4-Arm-PEG-20k-CM (~1.0 g, 0.050 mmol) was dissolved in DCM, and γ-amino-2-propanol-ester-α-TMSE-pemetrexed (23, ~140 mg, ~0.24 mmol), TEA (~121 mg, ~1.12 mmol), HOBt (~34 mg, ~0.25 mmol) and EDC (186 mg, ~1.12 mmol) were added into the reaction solution. The reaction mixture was stirred at room temperature 48 hours and HPLC analysis indicated that the reaction was almost complete.

The product was precipitated twice in a 1:1 IPA/Et$_2$O mixture and isolated by centrifugation. After drying via vacuum overnight, a white solid was obtained (~1.0 g, ~100% recovery). HPLC indicated that it was Compound 27 without any small molecule impurities.

Synthesis of 4-arm-PEG-20k-γ-isopropyl-ester-pemetrexed (Compound 28). To a DMF solution of 4-arm-PEG-20k-γ-isopropyl-ester-α-TMSE-pemetrexed (Compound 27, ~1.0 g) was added ~1.5 mL of 1.0M TBAF THF solution. The reaction mixture was stirred at room temperature for 18 hours and HPLC analysis indicated that the reaction was complete. The product was precipitated from a 1:1 IPA/Et$_2$O mixture three times and isolated by centrifugation. A white solid was obtained (~677 mg, ~67% recovery). HPLC and NMR confirmed that it was 4-arm-PEG-20k-γ-isopropyl-ester-pemetrexed (Compound 28), the drug substitution was ~32%.

Hydrolysis Studies of 4-arm-PEG-γ-Ester-Pemetrexed Conjugates in PBS Buffer

About 5 mg of each conjugate of interest was dissolved in ~10 mL of pH 7.4 PBS buffer. Each solution was placed into 10 HPLC vials and incubated at 37° C. HPLC was used to analyze both the conjugate and released pemetrexed. The half life ($t_{1/2}$) of each tested conjugate is provided in Table 1.

TABLE 1

Half Life of Tested Conjugate

| Compound | $t_{1/2}$ in PBS |
|---|---|
| 4-arm-PEG-10k-Ethyl-Ester-Pemetrexed (Compound 24a) | ~58 days |
| 4-arm-PEG-20k-Ethyl-Ester-Pemetrexed (Compound 24b) | ~56 days |
| 4-arm-PEG-40k-Ethyl-Ester-Pemetrexed (Compound 24c) | ~54 days |
| 4-arm-PEG-20k-Isopropyl-Ester-Pemetrexed (Compound 28) | ~80 days |

Example 3

Multiple Dose Maximum Tolerated Dose in a Low Folate Diet

The purpose of this study was to determine the maximum tolerated dose for pemetrexed (PMX), Compound 20a (from Example 1), Compound 20b (from Example 1), Compound 20c (from Example 1), and Compound 20d (from Example 1) in female SCID mice fed a low folate diet. All compounds were administered intravenously, once each day, for ten consecutive days.

Calculations were made to provide "dose equivalents" between PMX, Compound 20a, Compound 20b, Compound 20c and Compound 20d, which "dose equivalents" along with the "actual dose" administered are provided in Table 2. All dosages in this example are expressed in terms of "dose equivalents" and adjustments were made for excipients, salts and hydration state.

Pemetrexed (PMX) (MW 471.383/FW 597.488, 38.3% parent) was obtained from McKesson as a fine, lyophilized white powder. It was stored protected from light, in a sealed jar filled with desiccant, at room temperature. Dosing solutions were prepared fresh on each treatment day by dissolving the dry compound in 0.9% NaCl and vortexing for several seconds (~30 sec). The resulting top dose was a clear and colorless solution, with a pH of 7.11. Lower dosage levels were prepared by direct dilution of the top dose stock solution with 0.9% saline.

Compound 20a (MW 12906, 9.5% parent) was a fine, light brown powder. It was stored protected from light at −20° C. Dosing solutions were prepared fresh on each treatment day by dissolving the dry compound in 0.9% NaCl and vortexing for several seconds (~30 sec). The resulting top dose was a clear solution that was yellow in color, with a pH of 6.49. Lower dosage levels were prepared by direct dilution of the top dose stock solution with 0.9% saline.

Compound 20b (MW 23580, 4% parent) was a clumpy, light brown powder. It was stored protected from light at −20° C. Dosing solutions were prepared fresh on each treatment day by dissolving the dry compound in 0.9% NaCl and vortexing for several seconds (~30 sec). The resulting top dose was a clear solution that was yellow in color, with a pH of 5.74. Lower dosage levels were prepared by direct dilution of the top dose stock solution with 0.9% saline.

Compound 20c (MW 32697, 3.7% parent) was a clumpy, light brown powder. It was stored protected from light at −20° C. Dosing solutions were prepared fresh on each treatment day by dissolving the dry compound in 0.9% NaCl and vortexing for several seconds (~30 sec). The resulting top dose was a clear solution that was yellow in color, with a pH of 6.09. Lower dosage levels were prepared by direct dilution of the top dose stock solution with 0.9% saline.

Compound 20d (MW 45023, 2.7% parent) was a clumpy, light brown powder. It was stored protected from light at −20° C. Dosing solutions were prepared fresh on each treatment day by dissolving the dry compound in 0.9% NaCl and vortexing for several seconds (~30 sec). The resulting top dose was a clear solution that was yellow in color, with a pH of 5.02. Lower dosage levels were prepared by direct dilution of the top dose stock solution with 0.9% saline.

TABLE 2

Dose Equivalents and Actual Doses

| COMPOUND | DOSE EQUIVALENTS (MG/KG/INJ) | ACTUAL DOSE (MG/KG/INJ) |
|---|---|---|
| PMX | 500.00 | 500.00 |
| PMX | 250.00 2 | 50.00 |
| VEHICLE TREATED | 0.2 ML/20 G | NA |
| PMX | 60.00 | 60.00 |
| PMX | 15.00 | 15.00 |
| PMX | 3.75 | 3.75 |
| PMX | 1.00 | 1.00 |
| COMPOUND 20A | 15.00 | 157.89 |
| COMPOUND 20A | 3.75 | 39.47 |
| COMPOUND 20A | 1.00 | 10.53 |
| COMPOUND 20B | 15.00 | 375.00 |
| COMPOUND 20B | 3.75 | 93.75 |
| COMPOUND 20B | 1.00 | 25.00 |
| COMPOUND 20C | 15.00 | 405.41 |
| COMPOUND 20C | 3.75 | 101.35 |
| COMPOUND 20C | 1.00 | 27.03 |
| COMPOUND 20D | 15.00 | 555.56 |
| COMPOUND 20D | 3.75 | 138.84 |
| COMPOUND 20D | 1.00 | 37.04 |

Female SCID mice (HsdIcr:Ha (ICR)-Prkdc-scid) were obtained from Harlan. They were seven weeks old on Day 1 of the experiment. The mice in Groups 1 and 2 were fed irradiated Rodent Diet 5053 (LabDiet™). The mice in Groups 3 through 19 were fed irradiated Folic Acid Deficient Purina TestDiet supplemented with 1% succinylsufathiazol from 14 days prior to dosing until 14 days after dosing was completed, at which time the study was terminated and the mice were then euthanized. All groups received drinking water ad libitum. Mice were housed in static cages in clean rooms that provide H.E.P.A filtered air into the environment at 100 complete air changes per hour. All treatments, body weight determinations, and tumor measurements were carried out in the environment. The environment was controlled to a temperature range of 70°±2° F. and a humidity range of 30-70%. All mice were observed for clinical signs at least once daily. Mice found in obvious distress or in a moribund condition were euthanized. The study was carried out in an AAALAC accredited facility.

Treatments began on Day 1. All mice weighed ≥19.4 g at the initiation of therapy. Mean group body weights at first treatment were well-matched (range of group means, 21.0-23.7 g). Mice in Groups 3 through 19 were fed irradiated Folic Acid Deficient Purina TestDiet with 1% Succinylsufathiazol for 14 days prior to dosing as well as throughout the entire experiment. All mice were dosed according to individual body weight on the day of treatment (0.2 ml/20 g).

All mice were observed for clinical signs at least once daily. Mice were weighed on each day of treatment and at least three times weekly thereafter. Individual body weights were recorded three times weekly. Treatment-related weight loss in excess of 20% is generally considered unacceptably toxic. In this report, a dosage level is described as tolerated if treatment-related weight loss (during and two weeks after treatment) is <20%. Upon death or euthanasia, all mice were necropsied to provide a general assessment of potential cause of death and perhaps target organs for toxicity.

Pemetrexed—Normal Diet; Treatment with PMX was toxic at 500 and 250 mg/kg, resulting in maximum treatment-related body weight losses in excess of 30%. Lethality was 100% (5/5) at the 500 mg/kg dosage level. The maximum tolerated dose of PMX in mice fed a conventional diet was <250 mg/kg.

Pemetrexed—Low Folate Diet; Treatment with PMX was toxic at 60, 15 and 3.75 mg/kg, resulting in a maximum treatment-related body weight loss of 38-31%. The body weight nadir occurred on Day 10-12. Treatment with PMX at 60 and 15 mg/kg produced 100% (5/5) and 40% (2/5) treatment-related mortality. Common clinical signs observed in these groups were rough pelage and diarrhea. Common necropsy findings were bloated, air-filled stomachs, pale livers, and necrotic intestines. Treatment with PMX at 1 mg/kg was tolerated, resulting in a maximum treatment-related body weight loss of 12.8%, and no treatment-related mortality. The body weight nadir occurred on Day 12. A common clinical sign observed in this group was rough pelage, but nothing significant was noted at necropsy. The maximum tolerated dose of PMX in mice fed a folate deficient diet was 1 mg/kg.

Compound 20a—Low Folate Diet; Treatment with Compound 20a at 15 mg/kg was toxic, producing a 40% (2/5) incidence of treatment-related deaths and a mean maximum treatment-related body weight loss of 14.9%. The body weight nadir occurred on Day 8. Lost body weight was recovered in approximately 10 days. Treatment with Compound 20a at 3.75 and 1 mg/kg was tolerated, producing maximum treatment-related body weight losses of approximately 3.0%. Rough pelage was a common clinical sign. There was one death in the 1 mg/kg dose group on Day 5. At necropsy, this animal had a pale liver and bloated intestines. The study was terminated 14 days after the final treatment and the remaining animals were necropsied. Necropsy observations included bloated intestines and air filled stomachs. Based on the weight loss data at both dosage levels, it is not clear that the death in the 1 mg/kg group was truly treatment-related. The maximum tolerated dose of Compound 20a in mice fed a folate deficient diet was ~3.75 mg/kg.

Compound 20b—Low Folate Diet; Treatment with Compound 20b was well tolerated at 15, 3.75, and 1 mg/kg, producing no treatment-related mortality. Maximum treatment-related body weight loss was dose dependent and ranged from 16.9% to 1.8%. The body weight nadir occurred on Day 12 for the 15 mg/kg dose group and on Day 5 for the 3.75 and 1 mg/kg dose groups. Rough pelage was a common clinical sign. Nothing significant was noted at necropsy. The maximum tolerated dose of Compound 20b in mice fed a folate deficient diet was ~15 mg/kg based on body weight loss.

Compound 20c—Low Folate Diet; Treatment with Compound 20c was toxic at 15 mg/kg, producing a maximum treatment-related body weight loss of 18.8% and a 20% (1/5) incidence of treatment-related deaths. The body weight nadir occurred on Day 10 and lost weight was not recovered prior to study termination. Necrotic intestines were noted at necropsy of the mouse that was found dead. Treatment with Compound 20c was tolerated at 3.75 and 1 mg/kg, producing maximum treatment-related body weight losses of 1.4% and 4.8%, respectively. The body weight nadirs occurred on Days 5 and 10 for the 3.75 and 1 mg/kg dosage level groups respectively. Lost body weight was recovered in 2.2 and 5.5 days, respectively. Rough pelage was a common clinical sign. There were no significant findings upon necropsy. The maximum tolerated dose of Compound 20c in mice fed a folate deficient diet was between 15 and 3.75 mg/kg.

Compound 20d—Low Folate Diet; Treatment with Compound 20d was toxic at 15 mg/kg, producing 28.8% treatment-related body weight loss and a 40% (2/5) incidence of treatment-related deaths. The body weight nadir occurred on Day 15 and lost weight was not recovered prior to study termination. Rough pelage was a common clinical sign. Nothing significant was found at necropsy. Treatment with Compound 20d was tolerated at 3.75 and 1 mg/kg, resulting in no treatment-related mortality and treatment-related body weight losses of 4.5 and 0.9%, respectively. The body weight nadirs occurred on Day 5 for both groups and lost weight was recovered in 11.3 and 0.8 days, respectively. Rough pelage was a common clinical sign. Nothing significant was found at necropsy. The maximum tolerated dose of Compound 20d in mice fed a folate deficient diet was ~3.75 mg/kg.

A table summarizing the data is provided in Table 3.

TABLE 3

Summary of Results from a Multiple Dose Maximum Tolerated Dose (MTD) Study

| Treatment | Dose equivalents (mg/kg/inj) | Max. Mean Body Weight change during Rx (%) (range) | Day of Max. Mean Body Weight Loss | % Rx Related Deaths | Days of Deaths (s = surviving at study end) | MTD (mg/kg) |
|---|---|---|---|---|---|---|
| Vehicle | 0.2 ml/20 g | −1.7 (−12.4, +5.8) | 12 | 0 | s, s, s, s, s | n/a |
| Pemetrexed | 60 | −38.1 (−36.3, −38.8) | 10 | 100 | 13, 13, 11, 8, 11 | ~1 |
|  | 15 | −38.4 (−34.6, −40.3) | 10 | 40 | s, 12, 10, s, s |  |
|  | 3.75 | −30.7 (−25.9, −36.3) | 12 | 0 | s, s, s, s, s |  |
|  | 1 | −12.8 (−9.6, −16.5) | 12 | 0 | s, s, s, s, s |  |
| Compound 20a (10K) | 15 | −14.9 (−6, −19.9) | 8 | 40 | s, 9, 9, s, s | between 3.75-15 |
|  | 3.75 | −3.0 (−7.3, +3.2) | 8 | 0 | s, s, s, s, s |  |
|  | 1 | −3.4 (−16.5, +3) | 5 | 20 | 6, s, s, s, s |  |
| Compound 20b (20K) | 15 | −16.9 (−14.1, −20.5) | 12 | 0 | s, s, s, s, s | ~15 |
|  | 3.75 | −6.5 (−2.5, −12) | 5 | 0 | s, s, s, s, s |  |
|  | 1 | −1.8 (−6.4, +1.9) | 5 | 0 | s, s, s, s, s |  |
| Compound 20c (30K) | 15 | −22.0 (−8.2, −36.7) | 19 | 20 | s, s, 10, s, s | between 3.75-15 |
|  | 3.75 | −1.4 (−4, +1.4) | 5 | 0 | s, s, s, s, s |  |
|  | 1 | −4.8 (−0.4, −12.2) | 10 | 0 | s, s, s, s, s |  |
| Compound 20d (40K) | 15 | −28.8 (−26.1, −36.6) | 15 | 40 | 18, s, s, 2, s | between 3.75-15 |
|  | 3.75 | −4.5 (−8.3, +1.5) | 5 | 0 | s, s, s, s, s |  |
|  | 1 | −0.9 (−3.9, +3.4) | 5 | 0 | s, s, s, s, s |  |

Example 4

Single Dose Maximum Tolerated Dose Study and In Vivo Xenograft Study

Because of too much efficacy of daily dosing for ten days in a pilot xenograft study (likely due to the effects of repeated dosing), a single dose maximum tolerated dose study was conducted using a method similar to that provided in Example 3 in order to have a better dosing schedule for a comparative xenograft study. In this maximum tolerated dose study, only a single dose of each of pemetrexed, 4-arm-PEG$_{20K}$-γ-amide pemetrexed (Compound 20b), 4-arm-PEG$_{30K}$-γ-amide pemetrexed (Compound 20c), 4-arm-PEG$_{40K}$-γ-amide pemetrexed (Compound 20d), 4-arm-PEG-20k-ethyl-ester-pemetrexed (Compound 24b), 4-arm-PEG-40k-ethyl-ester-pemetrexed (Compound 24c) and 4-arm-PEG-20k-isopropyl-ester-pemetrexed (Compound 28) was administered intravenously. The results of this study are provided in Table 4.

TABLE 4

Summary of Body Weight Loss Following Treatment

| | Single dose MTD | tested dose (equiv) | BWL | day | treatment-related deaths | mean day of death |
|---|---|---|---|---|---|---|
| Pemetrexed | 50 | 50 | −9.7% | 2 | 0 | — |
| | | 80 | −3.8% | 2 | 0 | — |
| | | 120 | −4.1% | 2 | 0 | — |
| 4-Arm-PEG-40k-ethyl-ester-pemetrexed (Compound 24c) | 10 | 5 | −0.5% | 5 | 0 | — |
| | | 10 | −7.6% | 5 | 0 | — |
| | | 15 | −15.7% | 7 | 0 | — |
| 4-Arm-PEG-20k-isopropyl-ester-pemetrexed (Compound 28) | 10 | 10 | −7.3% | 9 | 0 | — |
| | | 18 | −6.6% | 5 | 0 | — |
| | | 25 | −9.1% | 7 | 0 | — |
| 4-Arm-PEG-20k-ethyl-ester-pemetrexed (Compound 24b) | 12 | 8 | — | — | 0 | — |
| | | 12 | −8.9% | 5 | 0 | — |
| | | 20 | −10.4% | 5 | 0 | — |
| 4-Arm-PEG$_{20K}$-γ-amide pemetrexed (Compound 20b) | 70 | 70 | −8.7% | 7 | 0 | — |
| | | 95 | −16.4% | 7 | 0 | — |
| | | 125 | −24.4% | 7 | 1 | 9 |
| 4-Arm-PEG$_{30K}$-γ-amide pemetrexed (Compound 20c) | <40 | 40 | −19.6% | 9 | 5 | 12 |
| | | 70 | −25.0% | 9 | 2 | 10.5 |
| | | 95 | −27.1% | 7 | 3 | 9 |
| | | 125 | −25.3% | 9 | 2 | 10.5 |
| 4-Arm-PEG$_{40K}$-γ-amide pemetrexed (Compound 20d) | ~40 | 40 | −12.6% | 7 | 0 | — |
| | | 60 | −20.8% | 9 | 0 | — |
| | | 90 | −21.4% | 9 | 1 | 12 |
| | | 125 | −21.8% | 6 | 5 | 7 |

Using the data from this single dose maximum tolerated dose study, xenograft studies using pemetrexed, 4-arm-PEG$_{20K}$-γ-amide pemetrexed (Compound 20b), 4-arm-PEG$_{23K}$-γ-amide pemetrexed (Compound 20c), 4-arm-PEG$_{40K}$-γ-amide pemetrexed (Compound 20d), 4-arm-PEG-20k-ethyl-ester-pemetrexed (Compound 24b), 4-arm-PEG-40k-ethyl-ester-pemetrexed (Compound 24c) and 4-arm-PEG-20k-isopropyl-ester-pemetrexed (Compound 28) were conducted in female athymic nu/nu mice. Briefly, for run of the experiment, a previously untreated group of 8-12 week old mice was intravenously administered a test article prepared in saline and diluted to appropriate concentrations to allow administration volumes of a maximum of 20 mL/kg. Each compound of interest was tested twice: once at 80% of the maximum tolerated dose and once at 50% of the maximum tolerated (maximum tolerated doses calculated on the single dose maximum tolerated dose study).

Mice were observed daily for clinical signs and body weights were recorded daily (except on weekend days) then biweekly until the end of study. Dosing was terminated for any group in which mean weight loss exceeded 20% or >10% of animals died. Moribund animals were euthanized. As of day 26 of the study (where the study design allows for up to sixty days of study), tumor volume for both pemetrexed and 4-arm-PEG$_{20K}$-γ-amide pemetrexed (Compound 20b), 4-arm-PEG$_{30K}$-γ-amide pemetrexed (Compound 20c), 4-arm-PEG$_{40K}$-γ-amide pemetrexed (Compound 20d), 4-arm-PEG-20k-ethyl-ester-pemetrexed (Compound 24b), 4-arm-PEG-40k-ethyl-ester-pemetrexed (Compound 24c) and 4-arm-PEG-20k-isopropyl-ester-pemetrexed (Compound 28) exhibited similar and significantly less tumor volume than saline control. Furthermore, treatment with the "amide versions" [i.e., 4-arm-PEG$_{20K}$-γ-amide pemetrexed (Compound 20b), pemetrexed (Compound 20c), 4-arm-PEG$_{40K}$-γ-amide pemetrexed (Compound 20d)] resulted in the lowest tumor volumes of all articles tested. Based on these results, the study will continue.

The invention(s) set forth herein has been described with respect to particular exemplified embodiments. However, the foregoing description is not intended to limit the invention to the exemplified embodiments, and the skilled artisan should recognize that variations can be made within the spirit and scope of the invention as described in the foregoing specification.

What is claimed is:

1. A conjugate according to Formula I:

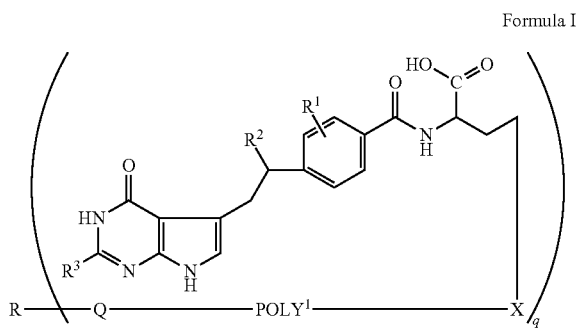

Formula I wherein:

R is a residue of pentaerythritol;

$R^1$ is H;

$R^2$ is H;

$R^3$ is amino;

Q is —O—;

POLY$^1$ is a poly(alkylene glycol);

X is —C(O)—NHCH$_2$CH$_2$(OCH$_2$CH$_2$)$_2$NH—C(O)—, —CH$_2$—C(O)—NHCH$_2$CH$_2$OCH$_2$CH$_2$O—C(O)—, or —CH$_2$—C(O)—NH—CH$_2$—CH(R$^4$)—O—C(O)—;

$R^4$ is H, —CH$_3$, —CH(CH$_3$)$_2$, —CH$_2$CH(CH$_3$)$_2$, or —CH(CH$_3$)CH$_2$CH$_3$; and q is 4;

and pharmaceutically acceptable salts and solvates thereof.

2. The conjugate of claim 1, wherein POLY$^1$ is a poly (ethylene oxide).

3. The conjugate of claim 1 according to Formula Ia:

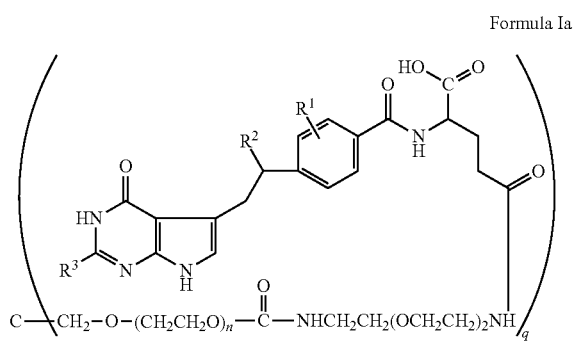

Formula Ia and pharmaceutically acceptable salts and solvates thereof, wherein each n is a positive integer from 10 to about 400.

4. The conjugate of claim 1, having the following structure:

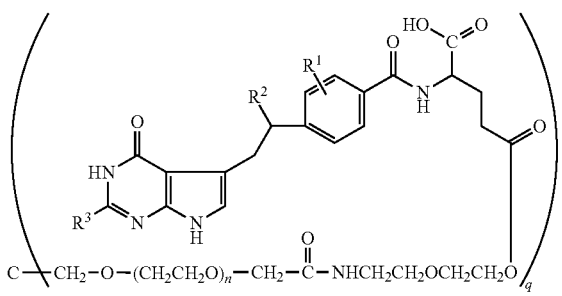

and pharmaceutically acceptable salts and solvates thereof, wherein each n is a positive integer from 10 to about 400.

5. The conjugate of claim 1, having the following structure:

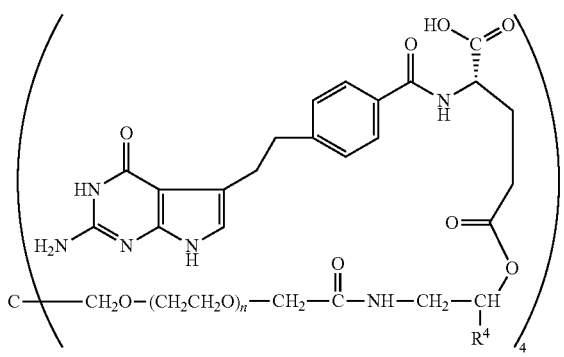

wherein:
each n is a positive integer from 10 to about 400;
and pharmaceutically acceptable salts and solvates thereof.

6. A composition comprising a plurality of conjugates, wherein at least 80% of the conjugates in the composition have a structure encompassed by claim 1.

7. The composition of claim 6, further comprising a pharmaceutical excipient.

* * * * *